(12) United States Patent
Gutman et al.

(10) Patent No.: US 7,947,740 B2
(45) Date of Patent: May 24, 2011

(54) BIMATOPROST CRYSTALLINE FORM I

(75) Inventors: Arie Gutman, Haifa (IL); Igor Rukhman, Haifa (IL); Boris Tishin, Haifa (IL); Lev Yudovich, Haifa (IL); Alexander Vilensky, Haifa (IL); Boris Pertsikov, Nesher (IL); Gennady Nisnevich, Haifa (IL)

(73) Assignee: Finetech Pharmaceutical Ltd, Nesher (IL)

( * ) Notice: Subject to any disclaimer, the term of this patent is extended or adjusted under 35 U.S.C. 154(b) by 254 days.

(21) Appl. No.: 11/896,002

(22) Filed: Aug. 29, 2007

(65) Prior Publication Data

US 2009/0163596 A1 Jun. 25, 2009

(30) Foreign Application Priority Data

Aug. 29, 2006 (IL) .......................................... 177762

(51) Int. Cl.
*A61K 31/165* (2006.01)
*C07C 235/34* (2006.01)
*C07C 231/24* (2006.01)
*A61P 27/02* (2006.01)
*C07F 7/18* (2006.01)

(52) U.S. Cl. .......................... 514/622; 564/171; 549/214

(58) Field of Classification Search ........................ None
See application file for complete search history.

(56) References Cited

U.S. PATENT DOCUMENTS

| 5,352,708 | A | 10/1994 | Woodward et al. |
| 2004/0171873 | A1 | 9/2004 | Gutman et al. |
| 2005/0154220 | A1 | 7/2005 | Clissold et al. |
| 2005/0209337 | A1 | 9/2005 | Gutman et al. |
| 2008/0145403 | A1* | 6/2008 | Spada et al. .................. 424/426 |

OTHER PUBLICATIONS

Morissette et al. High-throughput crystallization: polymorphs, salts, co-crystals and solvates of pharmaceutical solids. Adv. Drug Del. Rev. 56 (2004), 275-300.*
Vippagunta et al. Crystalline solids. Adv. Drug. Del. Rev. 48 (2001), 3-26.*
Easthope, et al (2002) "Topical Bimatoprost: A Review of its Use in Open-Angle Glaucoma and Ocular Hypertension." Drugs Aging 19 (3) 231-248.

* cited by examiner

*Primary Examiner* — Barbara P Badio
*Assistant Examiner* — Sara E Townsley
(74) *Attorney, Agent, or Firm* — Pearl Cohen Zedek Latzer, LLP; Mark S. Cohen

(57) ABSTRACT

The invention provides a novel polymorphic form I of crystalline bimatoprost, method for preparation thereof and new crystalline intermediates in the preparation. This form I of crystalline bimatoprost is used in purification of crude bimatoprost and in storage of bimatoprost as active pharmaceutical intermediate. Use of the physical form of bimatoprost in the manufacture of a medicament is also disclosed.

27 Claims, 14 Drawing Sheets

BIMATOPROST CRYSTALLINE FORM I

CROSS REFERENCE OF APPLICATION

This Application claims the benefit of Israeli Application Number 177762, filed Aug. 29, 2006, which is hereby incorporated by reference in its entirety.

FIELD OF THE INVENTION

The invention relates to novel polymorphic form I of crystalline bimatoprost, method for preparation thereof and new crystalline intermediates in the preparation. This form I of crystalline bimatoprost is used in purification of crude bimatoprost, and in storage of bimatoprost as active pharmaceutical intermediate. Use of the physical form of bimatoprost in the manufacture of a medicament is also disclosed.

BACKGROUND OF THE INVENTION

Elevated intraocular pressure (IOP) is the major risk factor associated with the etiology of glaucoma, a progressive optic neuropathy that can ultimately cause blindness. Prostamide analogs represent potent therapeutic agents in clinical management of glaucoma and other conditions associated with elevated intraocular pressure. The synthetic prostamide analog used to reduce IOP includes (9S,11R,15S)-9,11,15-trihydroxy-17-phenyl-18,19,20-trinor-5Z,13E-prostadienoic acid ethylamide

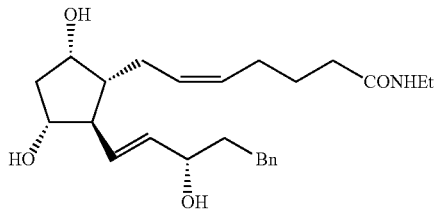

known under international nonproprietary name bimatoprost, currently marketed by Allergan as Lumigan™—0.03% bimatoprost ophthalmic solution for the treatment of open-angle glaucoma and ocular hypertension (*Drugs Aging*, 2002, 19, 231).

US2005/209337 discloses crystalline physical form of bimatoprost, which we designate as form A. The form is characterized by powder x-ray diffractometry, IR DRIFTS (KBr) spectroscopy, DSC and TGA. The present invention includes new polymorphic form of bimatoprost which is the most thermodynamically stable polymorph of bimatoprost and method for preparation thereof.

SUMMARY OF THE INVENTION

The present invention provides crystalline form I of bimatoprost and method for preparation thereof. The new crystalline form of bimatoprost is the most stable solid form of bimatoprost. Moreover, the new form of bimatoprost may be prepared so as to be substantially free of other physical forms.

The present invention also provides a method for purifying crude bimatoprost from related impurities, which comprises the steps of:

a) dissolving crude bimatoprost in an organic solvent or a mixture of organic solvent and anti-solvent at or near the boiling point;
b) allowing the hot solution to cool;
c) separating the precipitate from the supernatant solution;
d) drying the resulting solid in vacuo at low temperature and then at 30 to 40° C. to give purified bimatoprost in crystalline form I.

The present invention also provides the use of bimatoprost crystalline form I in the manufacture of a medicament. The medicament is prepared by combining a therapeutically effective amount of bimatoprost crystalline form I, as an active ingredient, with conventional pharmaceutically-acceptable excipients, e.g. an ophthalmically-acceptable vehicle, and by preparation of unit dosage forms suitable for pharmaceutical use, e.g. topical ocular use.

The present invention also provides new crystalline intermediate in the synthesis of bimatoprost—crystalline (3aR,4R,5R,6aS)-4-[3R-(t-butyldimethylsiloxy)-5-phenyl-1E-pentenyl]-5-(4-phenylbenzoyloxy)-hexahydro-2H-cyclopenta[b]furan-2-one 5a.

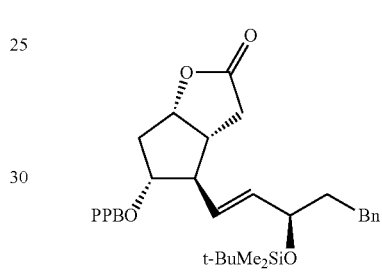

The crystalline intermediate is useful for complete isolation of desired crystalline (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one 5 as MTBE solvate

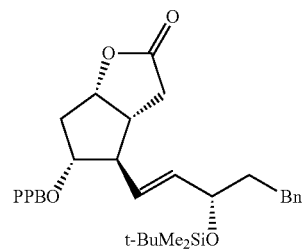

from reaction mixture and for recovery of by-product.

DETAILED DESCRIPTION OF THE INVENTION

US2005/209337 discloses crystalline physical form of bimatoprost, which we designate as form A. The present invention discloses, according to its first aspect, a new crystalline form of bimatoprost, which we designate as form I. Moreover, the bimatoprost crystalline form I may be prepared so as to be substantially free of other physical forms.

The present invention provides a process for producing crystalline form I substantially free from other physical forms of bimatoprost by crystallization of bimatoprost in any physical form from an organic solvent or from a mixture of organic solvent and anti-solvent. Preferably, the crystallization comprises the steps of:

a) dissolving crude bimatoprost in an organic solvent or a mixture of organic solvent and anti-solvent at or near the boiling point;
b) allowing the hot solution to cool;
c) separating the precipitate from the supernatant solution;
d) drying the resulting solid in vacuo at low temperature and then at 30 to 40° C. to yield bimatoprost crystalline form I substantially free from other physical forms.

The said organic solvent is selected from the group consisting of alcohols, esters, ketones, chloroorganic solvents, or mixture thereof. Preferably, said alcohols are selected from the group consisting of methanol, ethanol, isopropanol, butanol, isobutanol, t-butanol or mixture thereof. Preferably, said esters are selected from the group consisting of ethyl acetate, isopropyl acetate, butyl acetate or mixture thereof. Preferably, said ketones are selected from the group consisting of acetone, methyl ethyl ketone, isopropylacetone or mixture thereof. Preferably, said chloroorganic solvents are selected from the group consisting of dichloromethane, chloroform, chlorobenzene or mixture thereof.

The said anti-solvent is selected from the group consisting of hydrocarbons, ethers or mixture thereof. Preferably, the anti-solvent is saturated hydrocarbon. Preferably, said saturated hydrocarbon is selected from the group consisting of pentane, heptane, hexane, cyclohexane or mixture thereof. Preferably, said ethers are selected from the group consisting of diethyl ether, diisopropyl ether, MTBE or mixture thereof.

A pure crystalline organic compound has, in general, a definite melting point range. The melting point is defined as the point at which the sample is entirely in the liquid phase. Bimatoprost crystalline form I has a characteristic melting point range determined by the capillary method from 62 to 64° C.

Differential scanning calorimetry (DSC), x-ray powder diffraction (XRPD) and infrared (IR) spectroscopy were used to characterize the new form.

Figure 2:
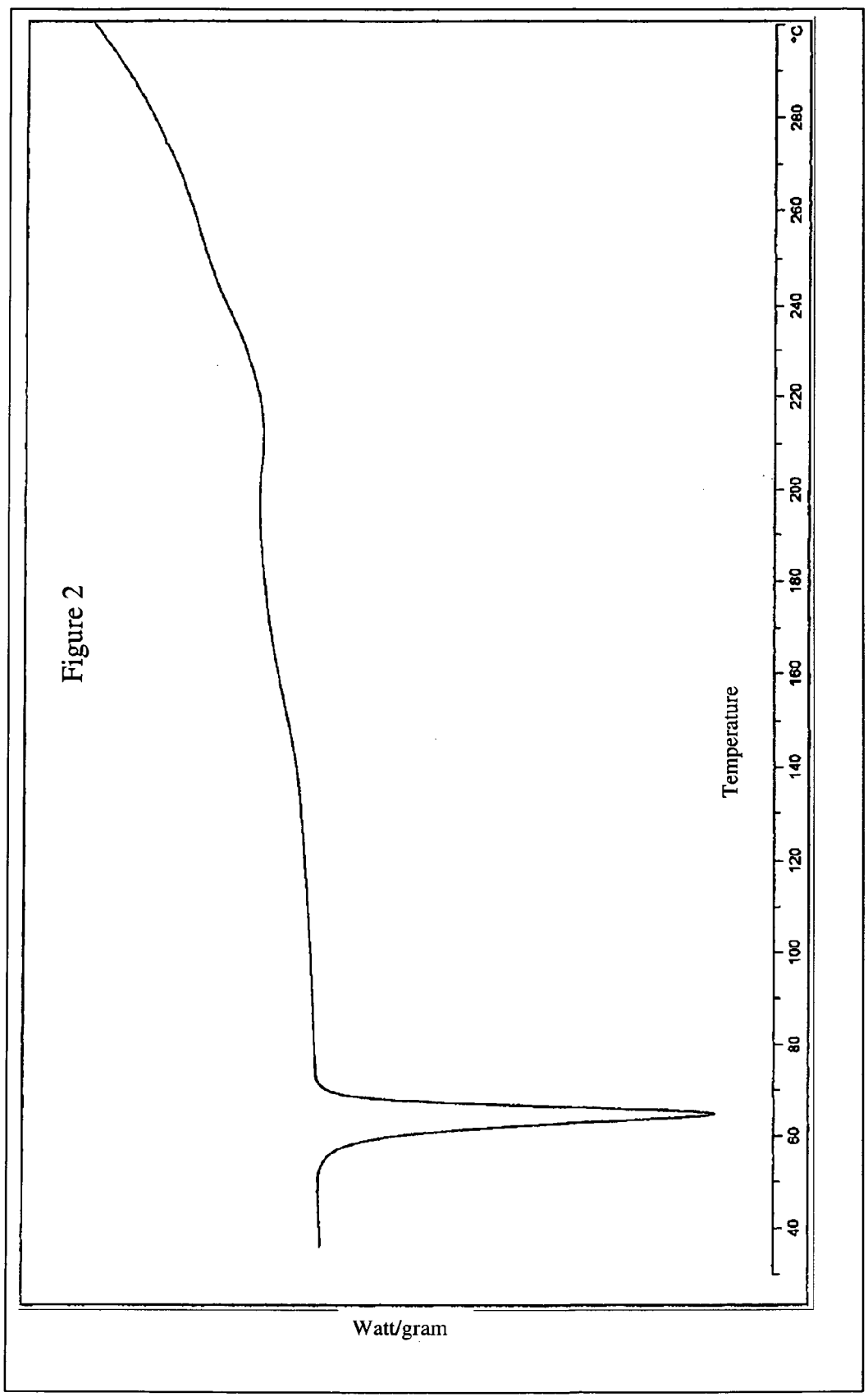
FIG. 2 shows the differential scanning calorimetry (DSC) curve of bimatoprost crystalline form I, according to embodiments of the invention.

The DSC curve of form I (FIG. 2) exhibits a melting endotherm at approximately 60-66° C.

Figure 1:
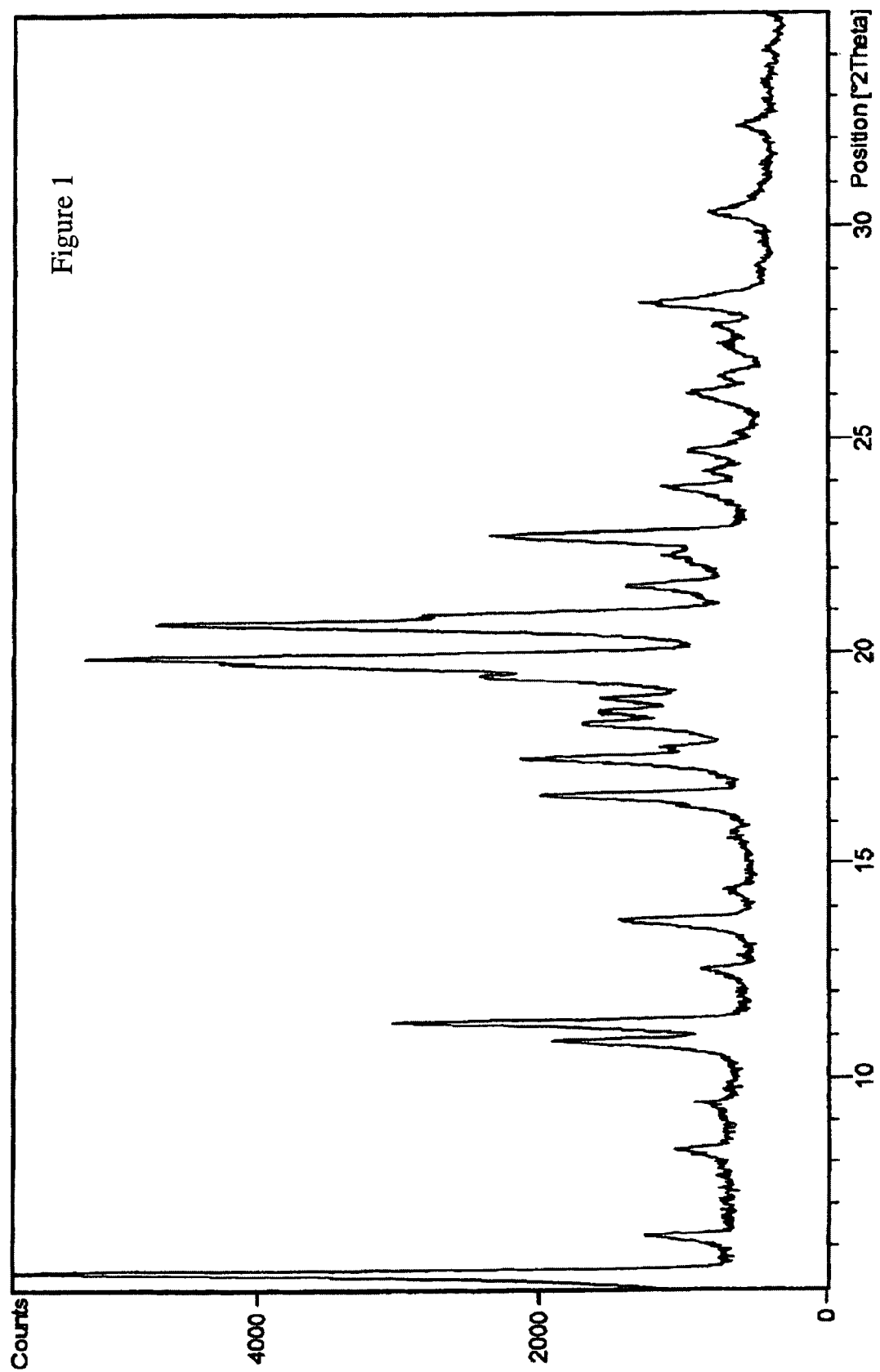
FIG. 1 shows a characteristic x-ray powder diffraction pattern of bimatoprost crystalline form I, according to embodiments of the present invention. Vertical axis: intensity (counts per second); Horizontal axis: 2θ (degrees).

Bimatoprost crystalline form I also exhibits distinctive x-ray powder diffraction pattern, as depicted in FIG. 1. The pattern has characteristic peaks expressed in degrees 2θ at approximately 5.4±0.2, 10.9±0.2, 11.3±0.2, 13.7±0.2, 16.6±0.2, 17.5±0.2, 19.9±0.2, 20.7±0.2 and 22.7±0.2.

Figure 3:
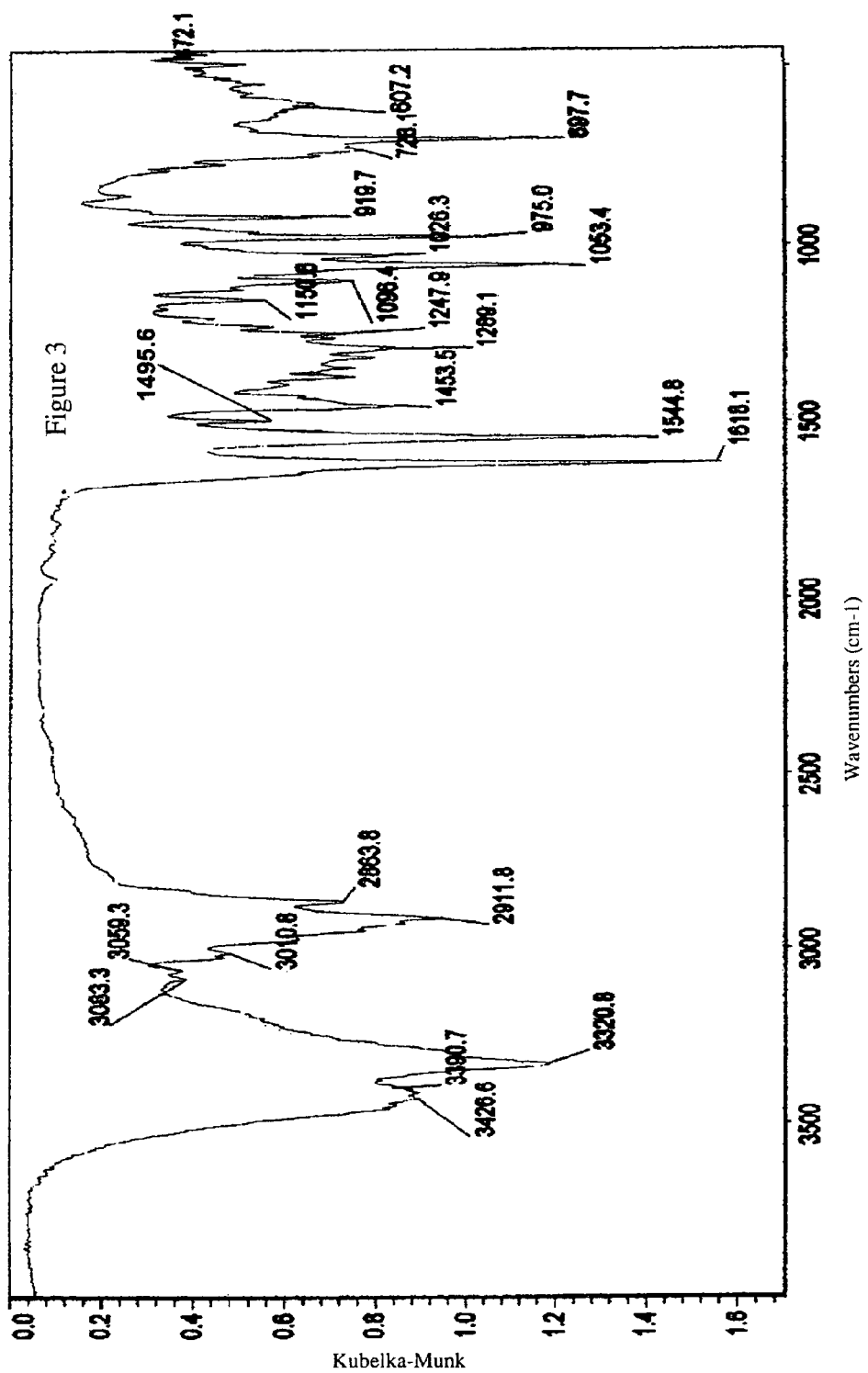
FIG. 3 shows the infrared spectrum (diffuse reflectance, DRIFTS) of bimatoprost crystalline form I in potassium bromide, according to embodiments of the invention.
Figure 4:
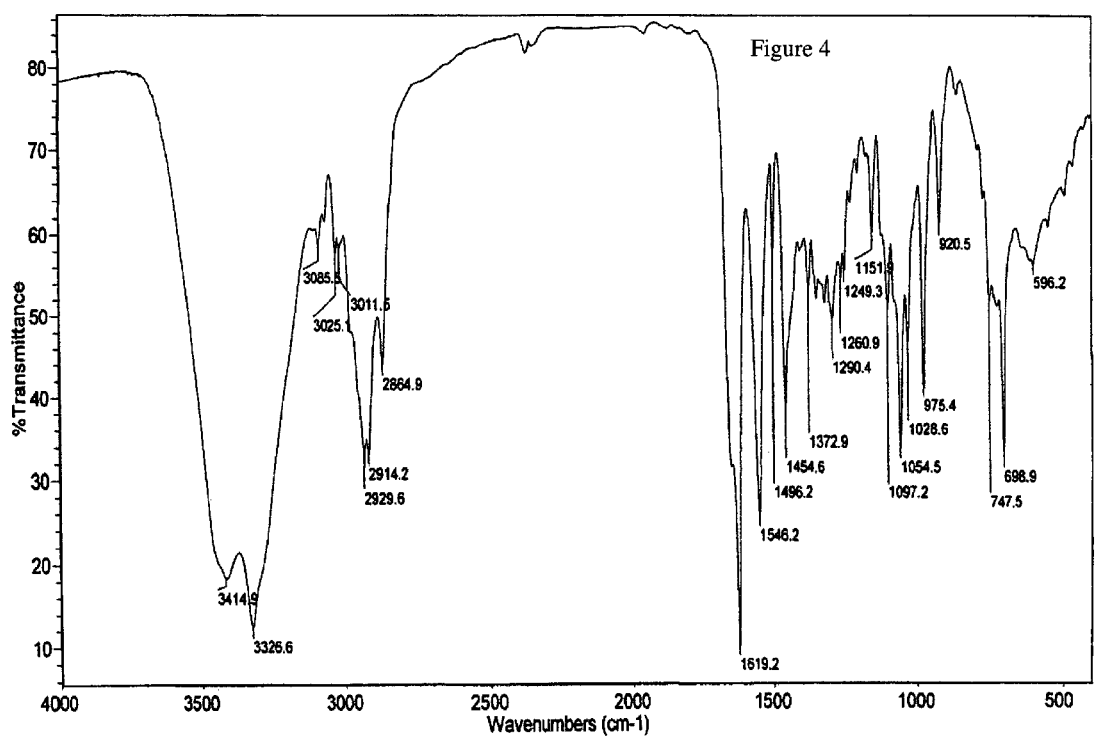
FIG. 4 shows the infrared spectrum of bimatoprost crystalline form I in potassium bromide, according to embodiments of the invention.
Figure 5:
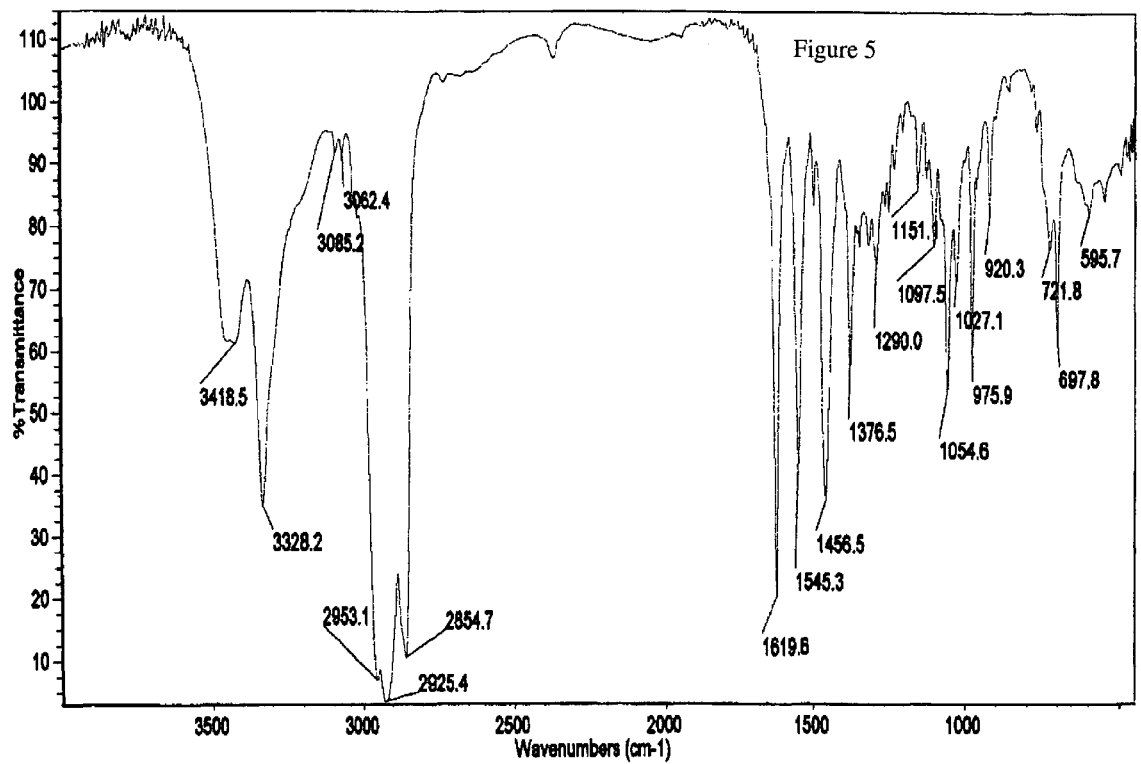
FIG. 5 shows the infrared spectrum of bimatoprost crystalline form I in Nujol, according to embodiments of the invention.
Figure 6:
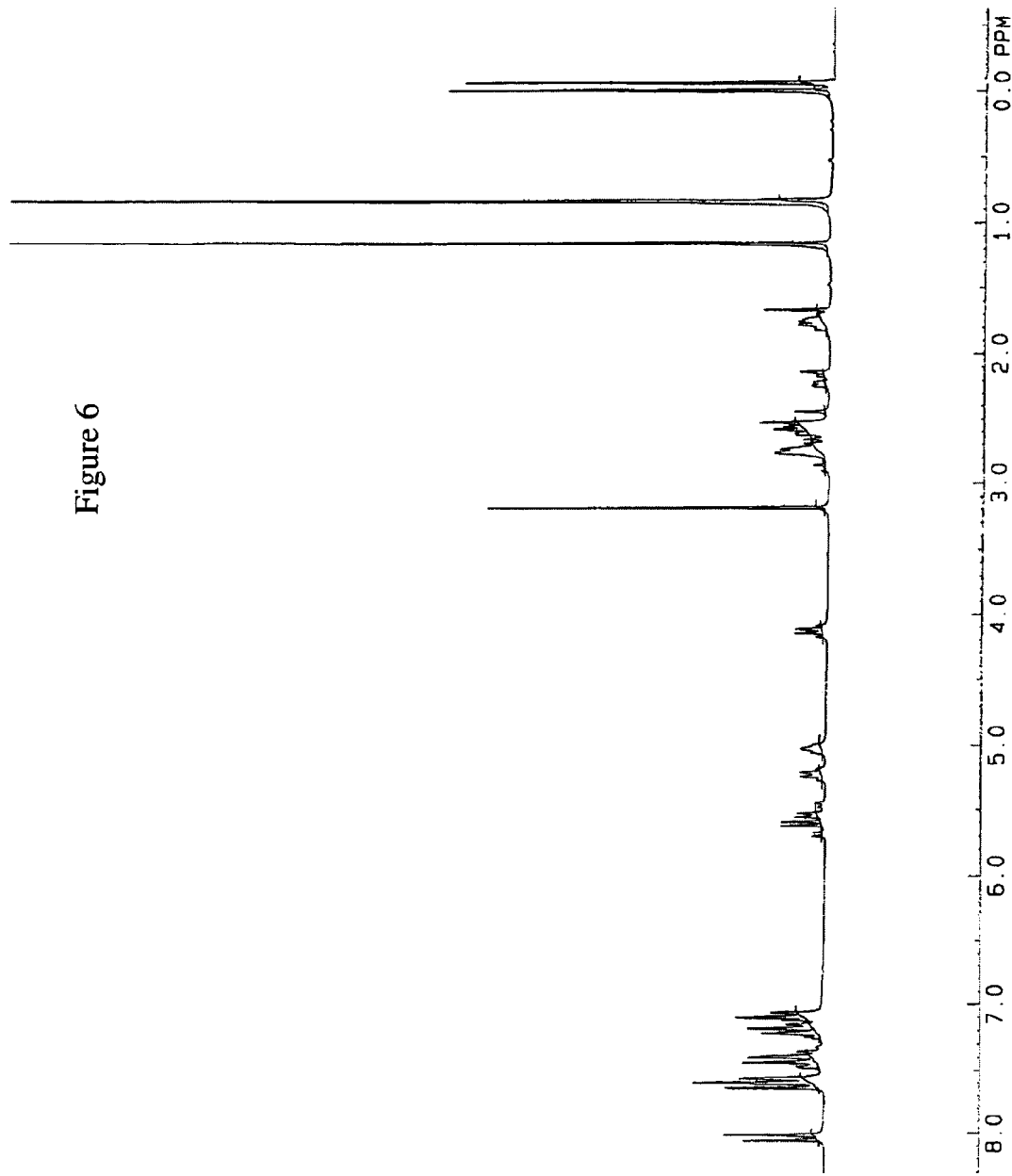
FIG. 6 shows the $^1$H nuclear magnetic resonance (NMR) spectrum of compound 5 MTBE solvate in CDCl$_3$, according to embodiments of the invention.

The crystalline form I was characterized by an infrared diffuse reflectance spectrum in potassium bromide as depicted in FIG. 3. The crystalline form I was further characterized by an infrared absorption spectrum carried out in potassium bromide and in Nujol as depicted in FIGS. 4 and 5.

Bimatoprost crystalline form I is the most stable crystalline modification of bimatoprost in a temperature range between −70 and +30° C. Stability data supports the retest period of not less than 6 months if bimatoprost crystalline form I is stored in an appropriate container at 2 to 8° C. and at 25° C.

The importance of bimatoprost crystalline form I rests primarily (but not exclusively) in its thermodynamic stability. Besides its greater stability, form I shows advantages with respect to form A because of the possibility of its preparation by crystallization employing different solvents in a wide temperature range. For example, the crystalline form I may be easily prepared by recrystallizing, triturating, or reslurring of crystalline form A.

Crude non-crystalline bimatoprost may be prepared by amidation of bimatoprost acid 3

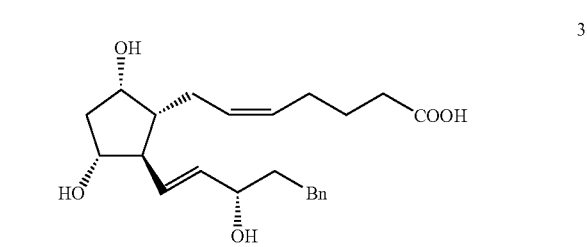

3 with ethylamine optionally in the presence of carbodiimides. Preferably, the carbodiimides are selected from the group of N,N-dicyclohexylcarbodiimide (DCC) and N-(3-dimethylaminopropyl)-N'-ethylcarbodiimide (EDC). Preferably, crude bimatoprost is prepared by reaction of bimatoprost acid methyl ester with ethylamine as described in US2004/171873, US2005/209337, US2005/154220 and US5352708.

Methyl ester of bimatoprost acid 2

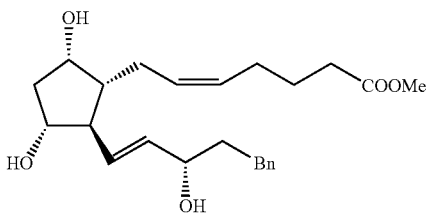

may be prepared by reacting of bimatoprost acid 3 with methylation agent MeY
wherein Y is a leaving group, in the presence of base.
Preferably, the methylation agent is methyl iodide, bromide, methanesulfonate, p-toluenesulfonate, 2, 4-dinitrophenylsulfonate or triflate.
Optionally, the base is 1, 8-diazabicyclo[5.4.0]undec-7-ene (DBU). Preferably, the base is $K_2CO_3$. Most preferably, the base is cesium carbonate, hydrogencarbonate, hydroxide or fluoride or mixture thereof. If cesium alkali is used as base in the methylation reaction cesium salt of bimatoprost acid

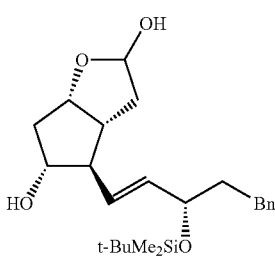

is obtained as intermediate in the reaction.
Preferably, the methylation reaction of bimatoprost acid 3 is provided in the presence of solvent. Preferably, the solvent is aprotic organic solvent. More preferably, the solvent is polar organic solvent. For example, the polar organic solvent is N,N-dimethylformamide (DMF), N,N-dimethylacetamide, 1-methyl-2-pyrrolidinone (NMP), dimethyl sulfoxide (DMSO), sulfolane or HMPA. Preferably the solvent is DMF. The bimatoprost acid methyl ester 2 prepared by the reaction may be used in following amination reaction without purification; however ester 2 may be purified by flash chromatography. Preferably the purification is provided by preparative LC on silica gel or Phenomenex™ Luna CN silica gel.

According to embodiment of the invention, the bimatoprost acid 2 is prepared by Wittig reacting of lactol

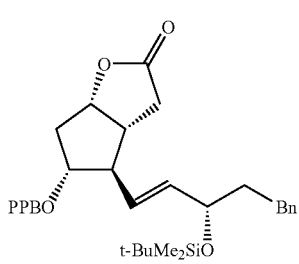

with a metal salt of 5-(triphenylphosphoranylidene)pentanoic acid following by desilylation of intermediate protected bimatoprost acid.

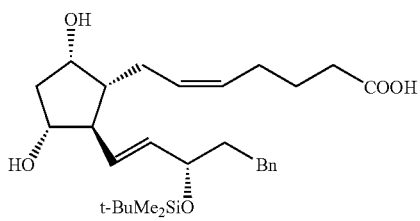

Preferably, the Wittig reaction is provided in the presence of aprotic organic solvent. More preferably, the solvent is ether-type solvent. Most preferably the solvent is THF. Analytical HPLC showed that crude bimatoprost acid 3 prepared by the Wittig reaction contains up to 5% of 5-trans isomer 3b.

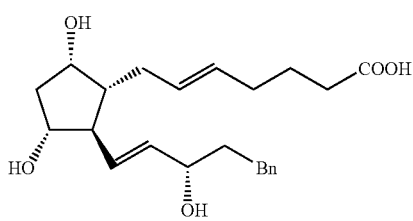

The lactol 4 may be prepared by reducing compound of formula

5

[structure 5]

wherein with i-$Bu_2AlH$ at temperature range from −80 to −50° C. Preferably, the reaction temperature range is −50 to +20° C., more preferably −30 to 0° C. To increase the yield of lactol 4 it is desirable to add i-$Bu_2AlH$ to lactone 5 at −50 to +20° C. (preferably at −30 to 0° C.) to attain about 95-99% conversion of lactone group. Preferably, the reaction is provided in the presence of aprotic organic solvent. More preferably, the solvent is toluene, $CH_2Cl_2$, THF, ether or mixture thereof.

The process of the present invention for the synthesis of bimatoprost may be summarized by the Scheme 1. Analytical HPLC showed that crude bimatoprost 1 prepared according to Scheme 1 contains up to 5% of 5-trans isomer 1b (from the Wittig reaction).

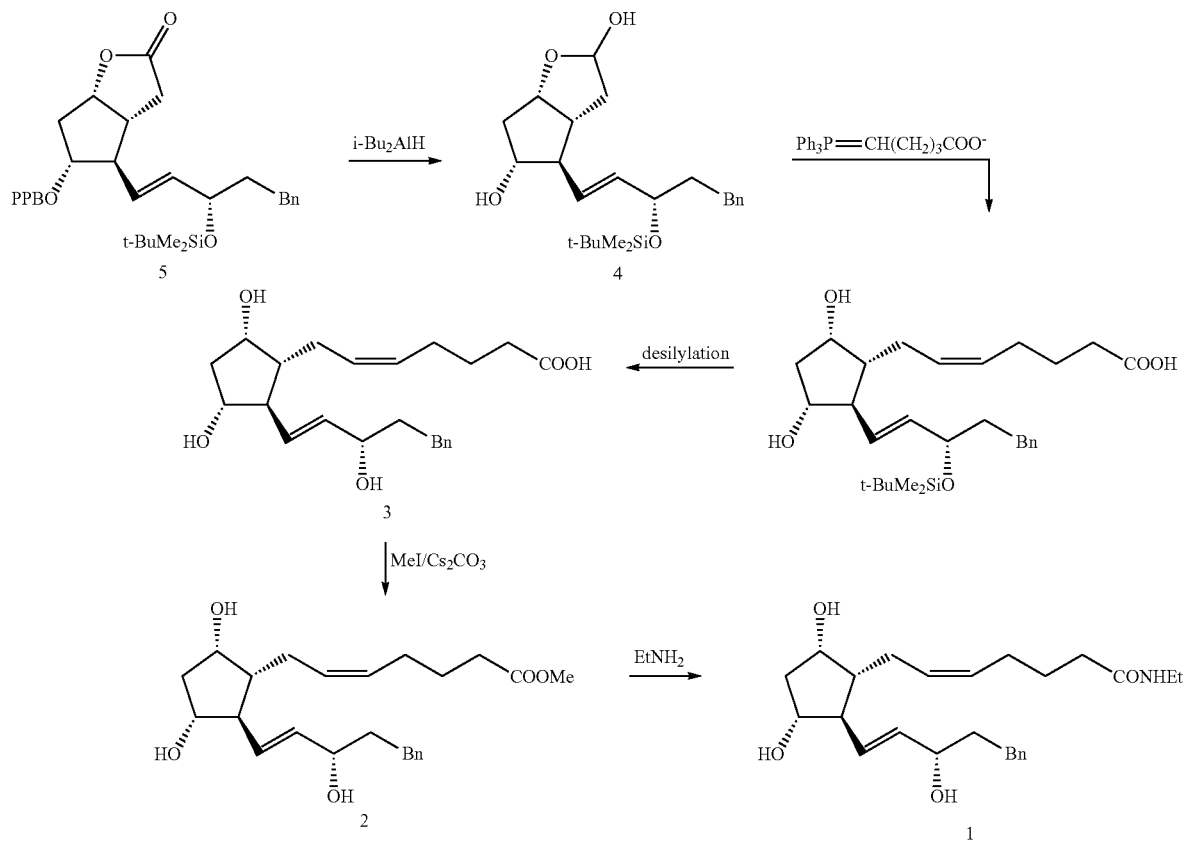
Scheme 1
In one embodiment of the invention, the lactone 5 is prepared by process comprising: reduction of the carbonyl group of ketone 7
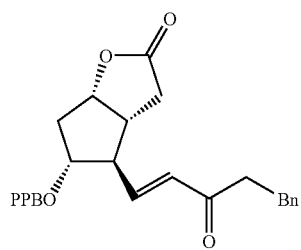
7
to yield a mixture of compounds of formulae 6 and 6a
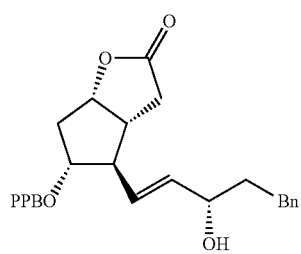
6
-continued
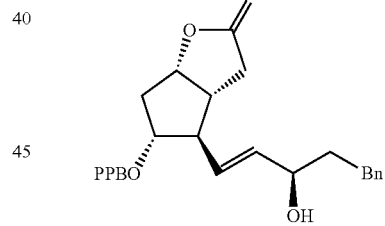
6a
which are subsequently converted into a mixture of compounds 5 and
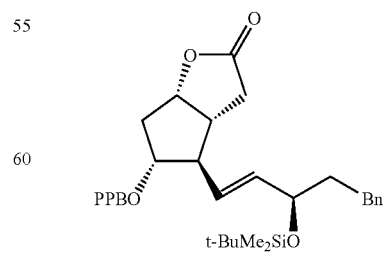
5a
followed by isolation of the compounds 5 and 5a from the mixture.

The process for the synthesis of compound 5 from enone 7 may be summarized by the following Scheme 2:

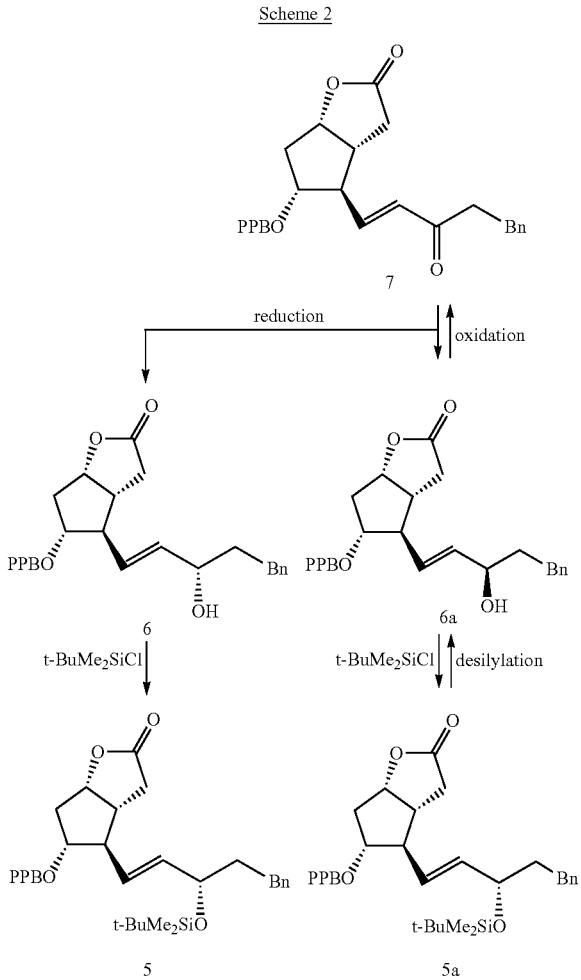

Basis of the synthesis is easy separation of lactone 5 as crystalline MTBE solvate from mixture of 5 and 5a isomers. The potential of the separation method may be illustrated by isolation of highly pure lactone 5 as MTBE solvate with 40% recovery and lactone 5a as solvent free crystalline compound with 33% recovery by serial of simple crystallizations of 1:1 mixture of 5 and 5a isomers from MTBE and hydrocarbon solvent.

The reduction of the compound 6 may be carried out with any reagent capable to reduce ketone function to alcohol. An example of the reagent is $NaBH_4$ or $(i\text{-PrO})_3Al$. Preferably the reduction of the compound 6 is carried out with (−)-B-chlorodiisopinocampheylborane or with borane in the presence of 2-alkyl-CBS-oxazaborolydines. More preferably the reduction is carried out with (−)-B-chlorodiisopinocamphenylborane in organic solvent. Preferably the organic solvent is THF, ether, 1,2-dimethoxyethane, toluene, hexane, $CH_2Cl_2$ or mixtures of these solvents.

In another embodiment of the invention, the invention provides crystalline MTBE solvate of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one 5

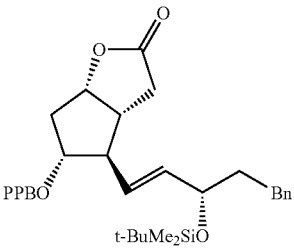

Crystalline MTBE solvate of lactone 5 has a characteristic melting point range determined by the capillary method from 60 to 64° C.

Differential scanning calorimetry (DSC), x-ray powder diffraction (XRPD) and infrared (IR) spectroscopy were used to characterize the new form.

Figure 9:
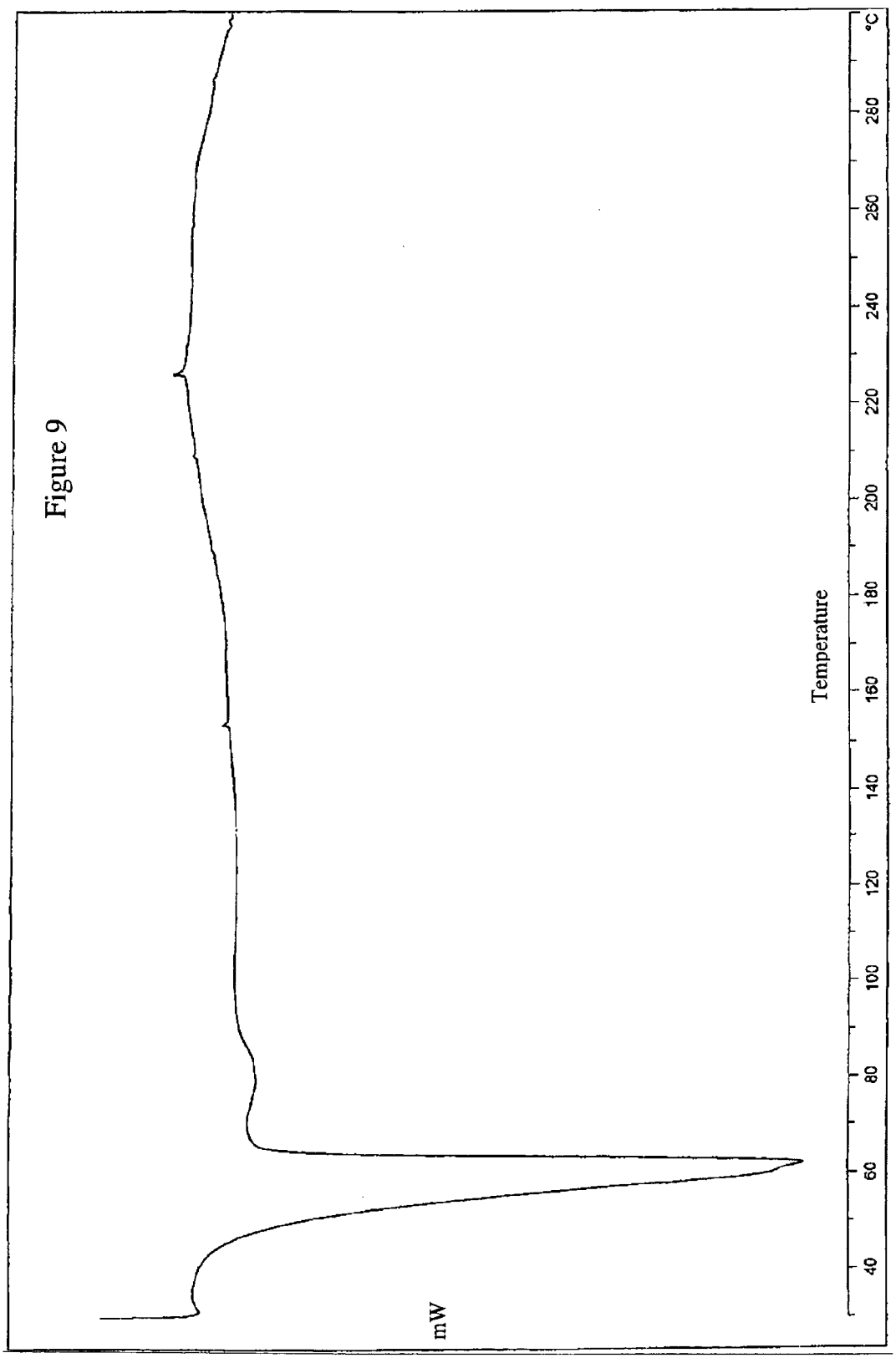
FIG. 9 shows the differential scanning calorimetry (DSC) curve of compound 5 MTBE solvate, according to embodiments of the invention.
Figure 10:
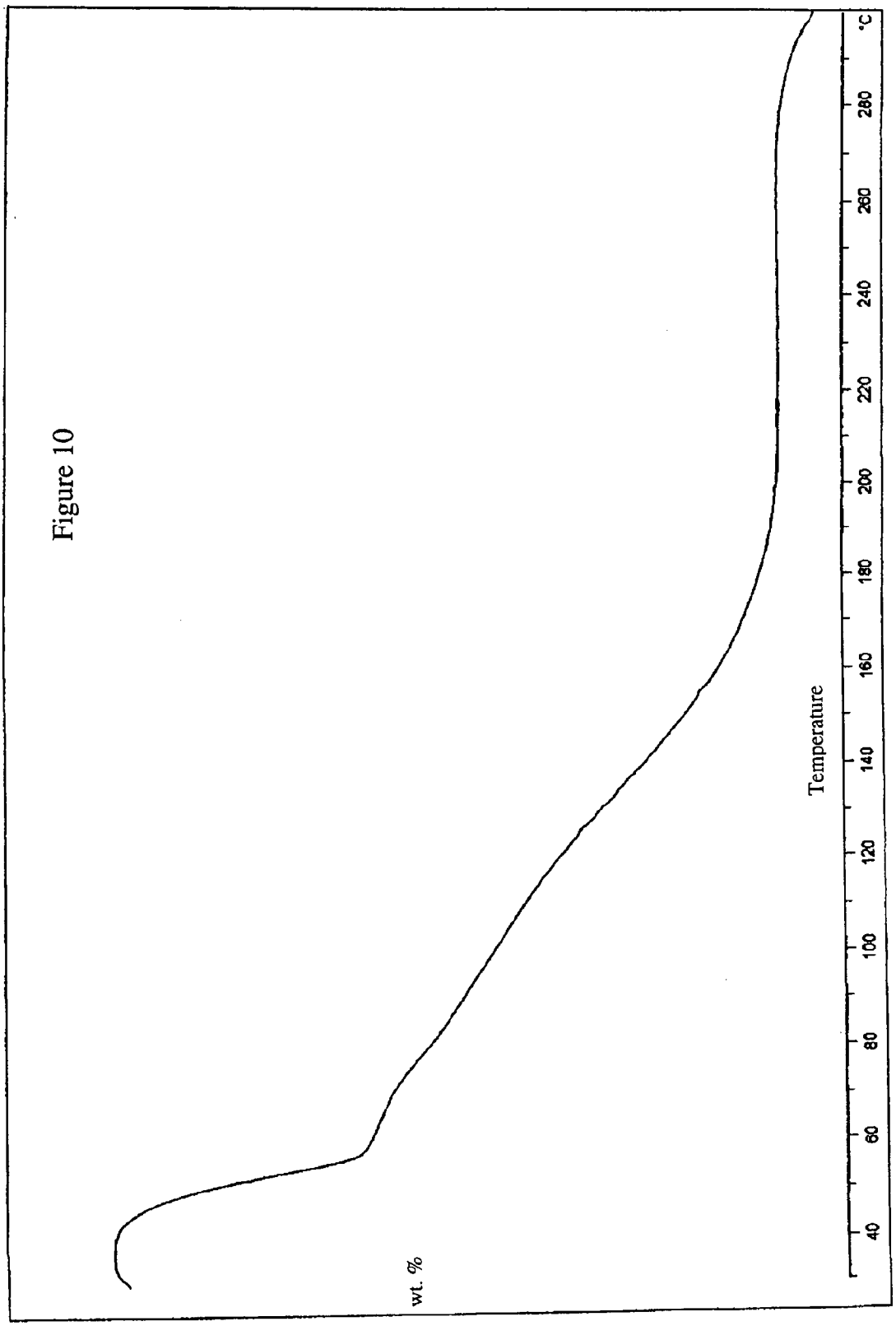
FIG. 10 shows the thermograviometric (TGA) curve of compound 5 MTBE solvate, according to embodiments of the invention.

Crystalline lactone 5 MTBE solvate (FIG. 9) exhibits a melting endotherm at approximately 60-66° C.

Figure 7:
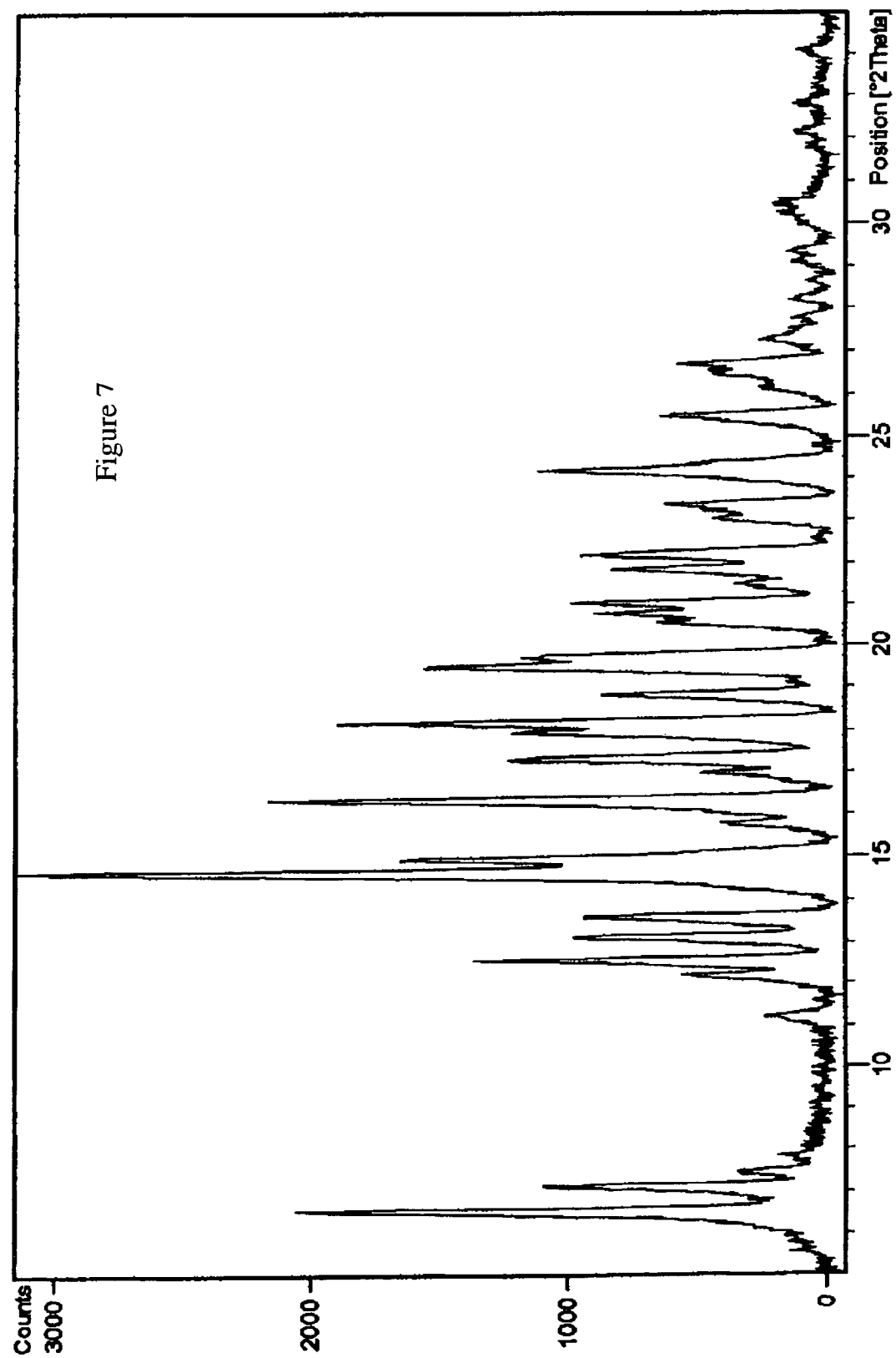
FIG. 7 shows a characteristic x-ray powder diffraction pattern of compound 5 MTBE solvate, according to embodiments of the present invention. Vertical axis: intensity (counts per second); Horizontal axis: 2θ (degrees).

Crystalline lactone 5 MTBE solvate also exhibits distinctive x-ray powder diffraction pattern, as depicted in FIG. 7. The pattern has characteristic peaks expressed in degrees 2θ at approximately 6.5±0.2, 7.1±0.2, 12.2±0.2, 12.5±0.2, 13.1±0.2, 13.6±0.2, 14.6±0.2, 15.0±0.2, 15.8±0.2, 16.2±0.2, 16.3±0.2, 17.0±0.2, 17.3±0.2, 18.0±0.2, 18.2±0.2, 18.8±0.2, 19.5±0.2, 19.7±0.2, 20.5±0.2, 20.8±0.2, 21.0±0.2, 21.8±0.2, 22.2±0.2, 23.0±0.2, 23.3±0.2, 24.2±0.2, 25.5±0.2, 26.5±0.2 and 26.7±0.2.

Figure 8:
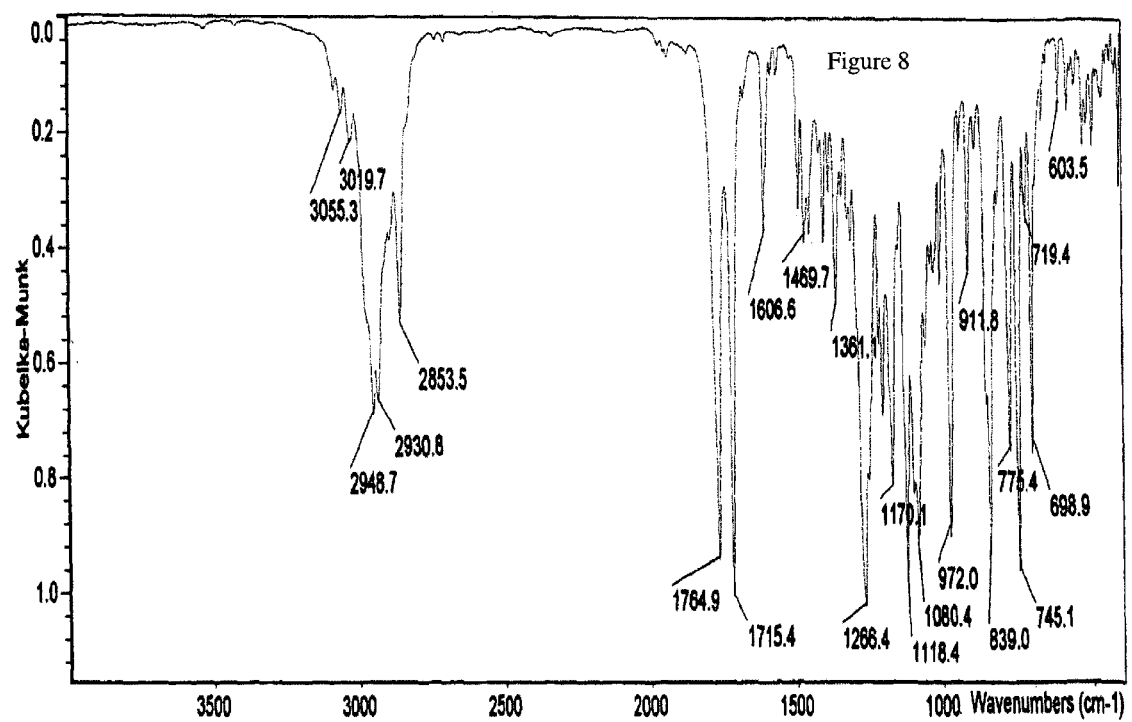
FIG. 8 shows the infrared spectrum (diffuse reflectance, DRIFTS) of compound 5 MTBE solvate in potassium bromide, according to embodiments of the invention.
Figure 11:
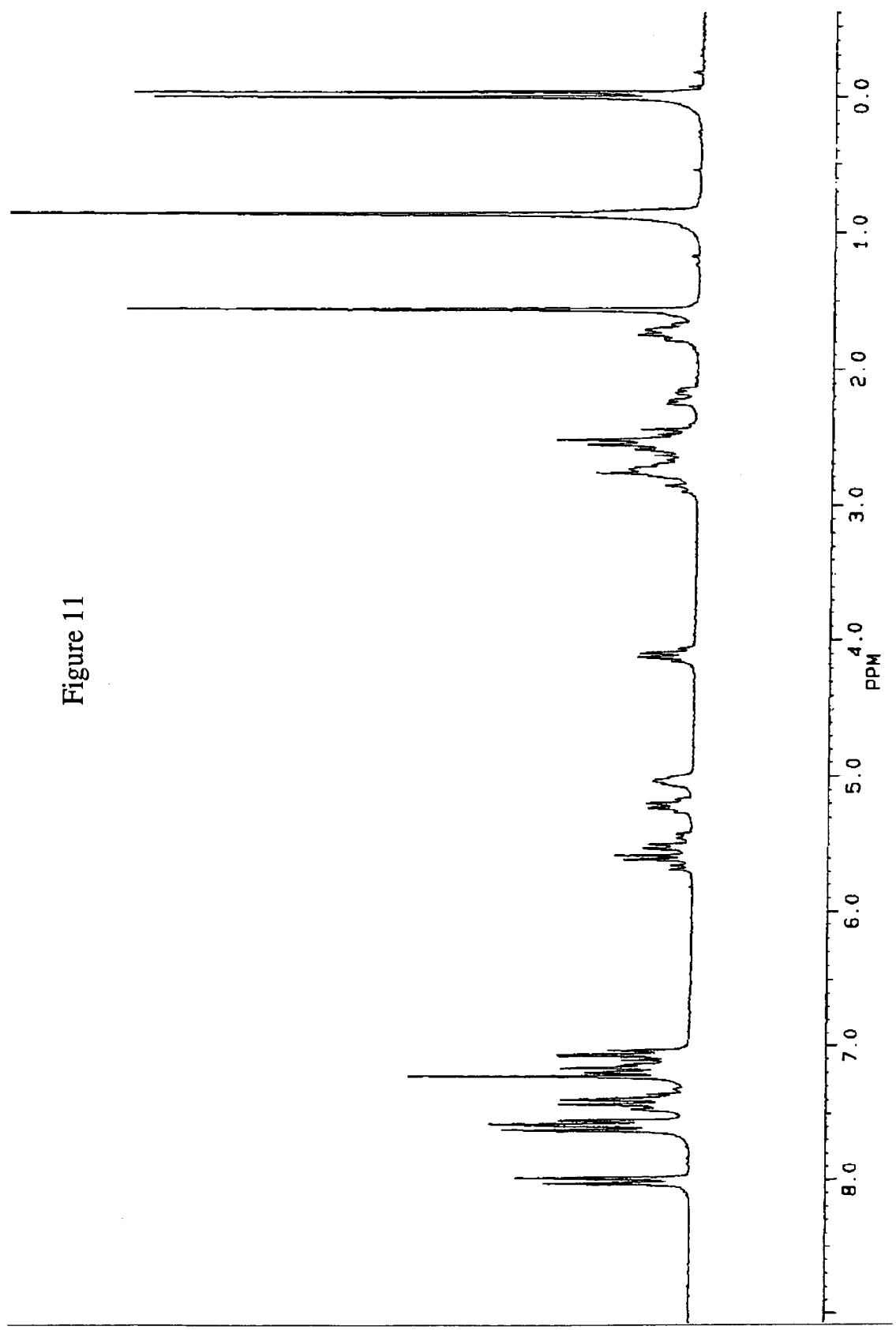
FIG. 11 shows the $^1$H nuclear magnetic resonance (NMR) spectrum of compound 5a in CDCl$_3$, according to embodiments of the invention.

The crystalline lactone 5 MTBE solvate was characterized by an infrared diffuse reflectance spectrum in potassium bromide as depicted in FIG. 8. The crystalline lactone 5 MTBE solvate was further characterized by $^1H$ NMR spectrum carried out in $CDCl_3$ as depicted in FIG. 11.

In another embodiment of the invention, the invention further provides crystalline (3aR,4R,5R,6aS)-4-[3R-(t-butyldimethylsiloxy)-5-phenyl-1E-pentenyl]-5-(4-phenylbenzoyloxy)-hexahydro-2H-cyclopenta[b]furan-2-one 5a.

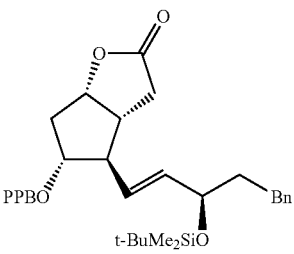

Crystalline lactone 5a has a characteristic melting point range determined by the capillary method from 93 to 94° C.

Figure 14:
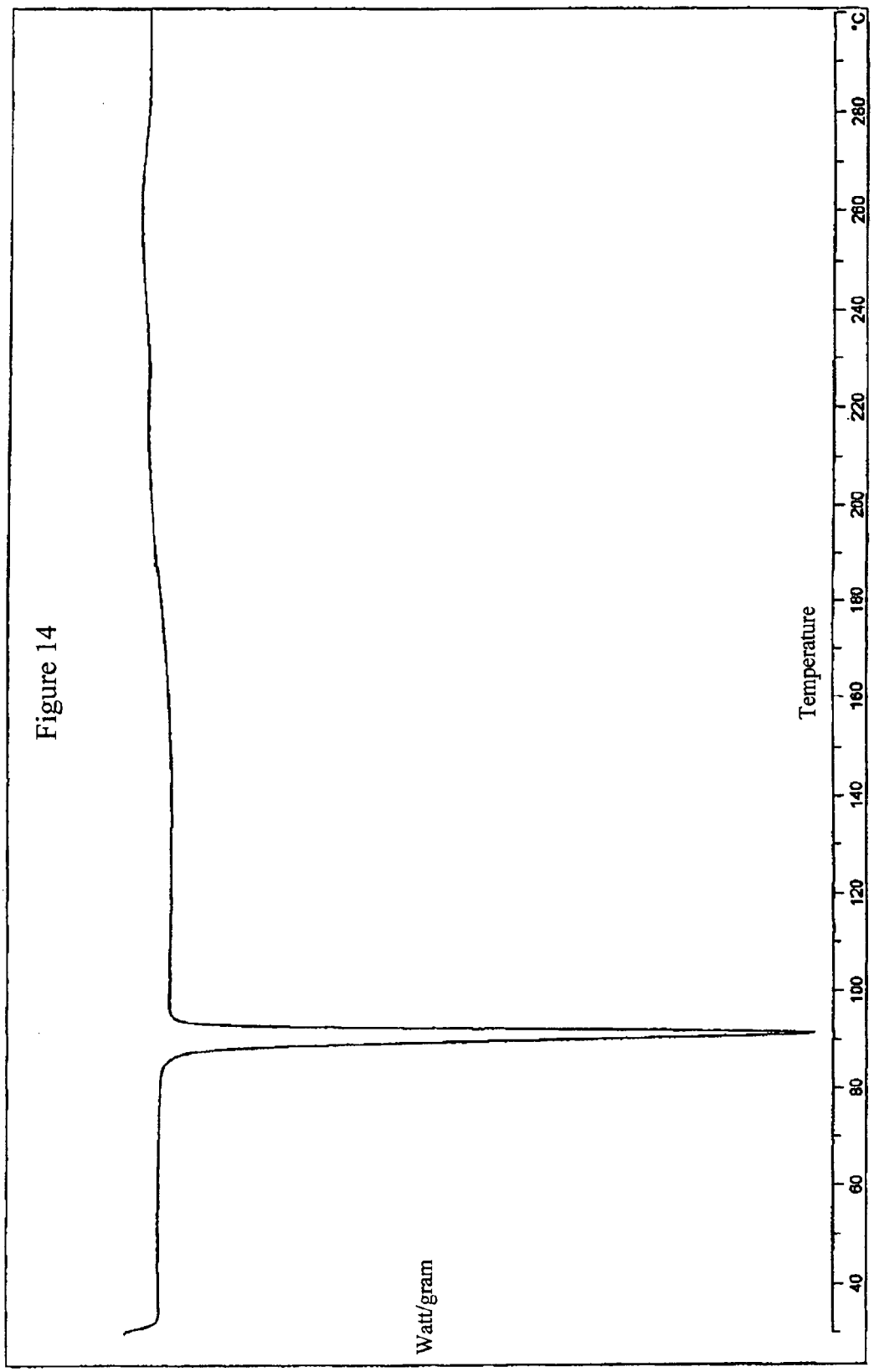
FIG. 14 shows the differential scanning calorimetry (DSC) curve of compound 5a, according to embodiments of the invention.

Crystalline lactone 5a (FIG. 14) exhibits a melting endotherm at approximately 83-97° C.

Figure 12:
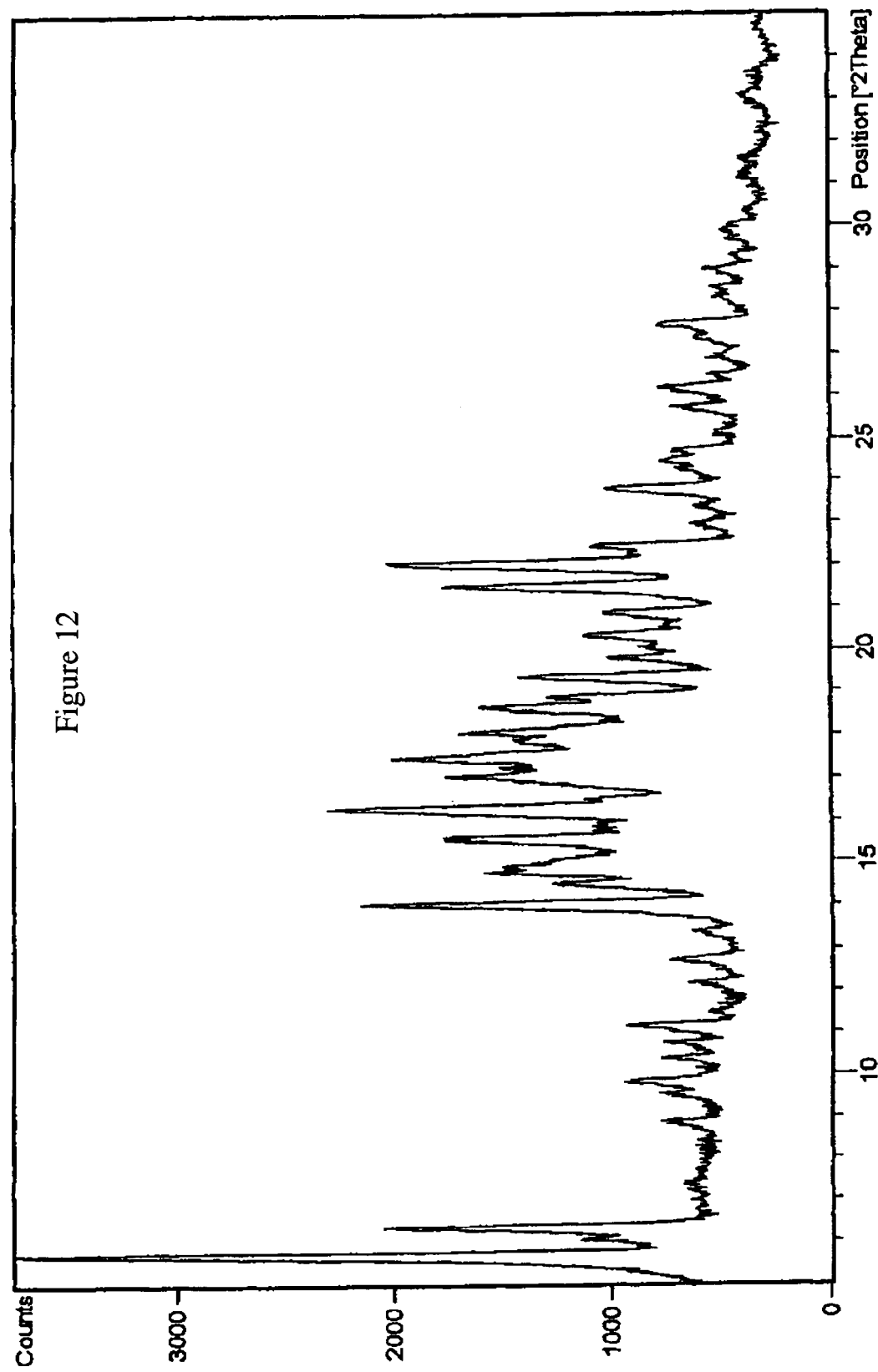
FIG. 12 shows a characteristic x-ray powder diffraction pattern of compound 5a, according to embodiments of the present invention. Vertical axis: intensity (counts per second); Horizontal axis: 2θ (degrees).
Figure 13:
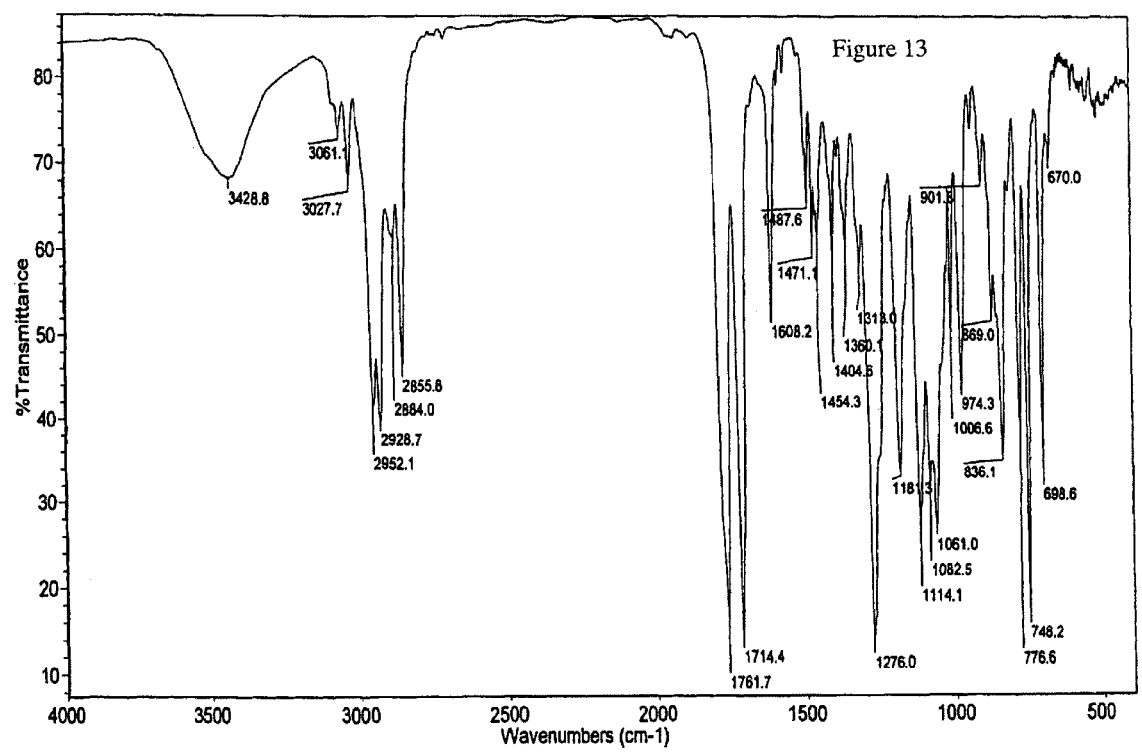
FIG. 13 shows the infrared spectrum (KBr) of compound 5a in potassium bromide, according to embodiments of the invention.

Crystalline lactone 5a also exhibits distinctive x-ray powder diffraction pattern, as depicted in FIG. 12. The pattern has characteristic peaks expressed in degrees 2θ at approximately 5.7±0.2, 6.3±0.2, 14.0±0.2, 14.5±0.2, 14.8±0.2, 15.5±0.2, 16.3±0.2, 17.0±0.2, 17.5±0.2, 17.8±0.2, 18.1±0.2, 18.6±0.2, 18.9±0.2, 19.3±0.2, 21.5±0.2, 22.0±0.2, 22.4±0.2 and 23.8±0.2.

Lactone 5a was characterized by $^1$H NMR (CDCl$_3$), powder x-ray diffractometry, DSC, and IR (KBr) spectroscopy as set forth above and illustrated in FIGS. 11-14. Crystallinity of compounds 5 (as MTBE solvate) and 5a give very rare option to isolate the compounds in highly pure form with high yield from 5/5a 1:1 mixture by simple crystallization procedure.

In another embodiment of the invention, it is proposed process for utilization of undesired compound 5a to compound 7 which process comprises the steps of converting compound 5a into compound 6a and oxidizing the hydroxyl group of the compound 6a.

According to embodiment of the invention, the compound of the formula 7 may be prepared by Homer-Emmons-Wadsworth reaction of Corey aldehyde of formula 8

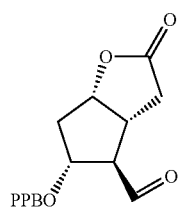

8 with a □-ketophosphonate BnCH$_2$COCH$_2$PO(OMe)$_2$ in the presence of base. Preferably, the base is BuLi, NaH or Et$_3$N/LiCl. More preferably, the base is alkali. For example the alkali is LiOH, NaOH, KOH, CsOH, Na$_2$CO$_3$, K$_2$CO$_3$ or Cs$_2$CO$_3$. Most preferably, the base is an aqueous alkali. Preferably, the Horner-Emmons-Wadsworth reaction is provided in the presence of organic solvents. For example, the solvent is CH$_2$Cl$_2$, CHCl$_3$, toluene, THF, MTBE, ether or mixture thereof.

According to embodiment of the invention, Corey aldehyde 8 may be prepared by oxidation of (−)-Corey lactone 5-(4-phenylbenzoate) of formula 9

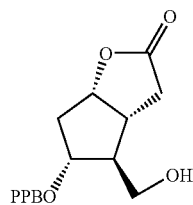

9

The oxidation of (−)-Corey lactone 5-(4-phenylbenzoate) 9 may be carried out with any oxidizing system capable to oxidize primary alcohol to aldehyde. An example of the oxidizing system is CrO$_3$/C$_5$H$_5$N, Cl$_2$/PhSMe, DMSO/DCC/H$^+$, or Dess-Martin reagent. Preferably, the oxidizing system is aq NaClO/TEMPO, more preferably aq NaClO/TEMPO/NaBr, most preferably NaClO/TEMPO/NaBr/i-PrOH.

The process for the synthesis of enone 7 from (−)-Corey lactone 5-(4-phenylbenzoate) 9 may be summarized by the following Scheme 3:

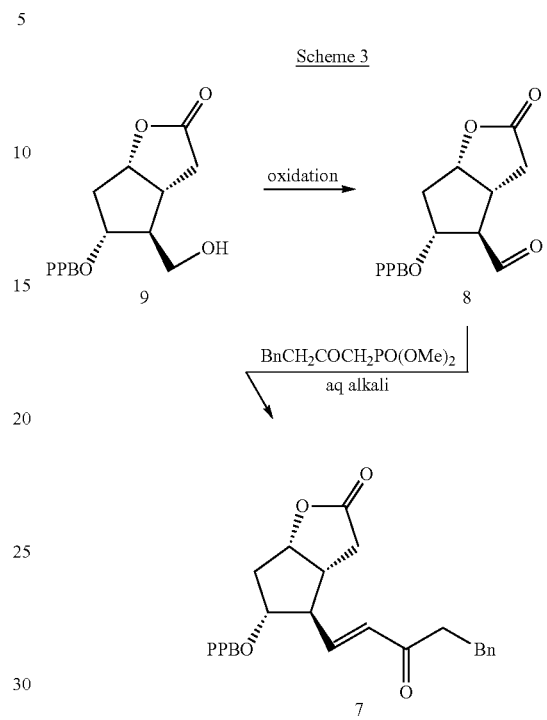

The major related impurities in bimatoprost that can be formed during synthesis or storage of bimatoprost, included the following:

methyl ester of bimatoprost acid 2:

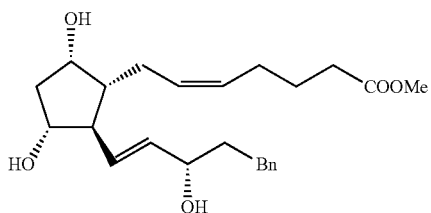

2 bimatoprost acid 3:

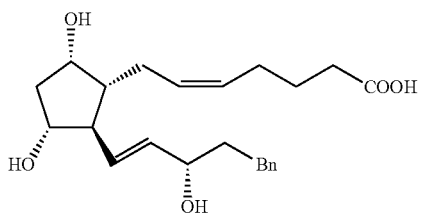

3

5-trans bimatoprost 1b:

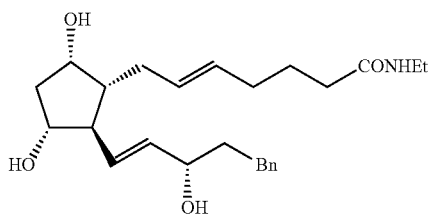

15(R) bimatoprost 1a:

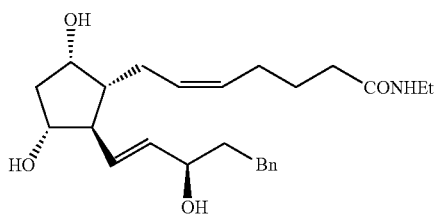

15-keto bimatoprost 1c:

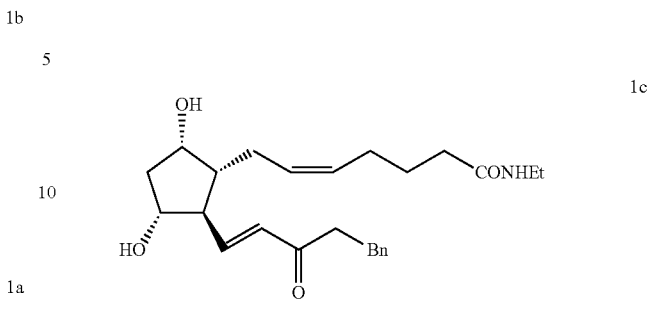

As mentioned above, impurities 5-trans bimatoprost 1b, 15R-bimatoprost 1a, 15-keto bimatoprost 1c could be formed during synthesis or storage of bimatoprost. These compounds were synthesized as analytical markers for HPLC analysis and characterized. We prepared 15R-bimatoprost 1a from lactone 5a according to Scheme 4.

Scheme 4

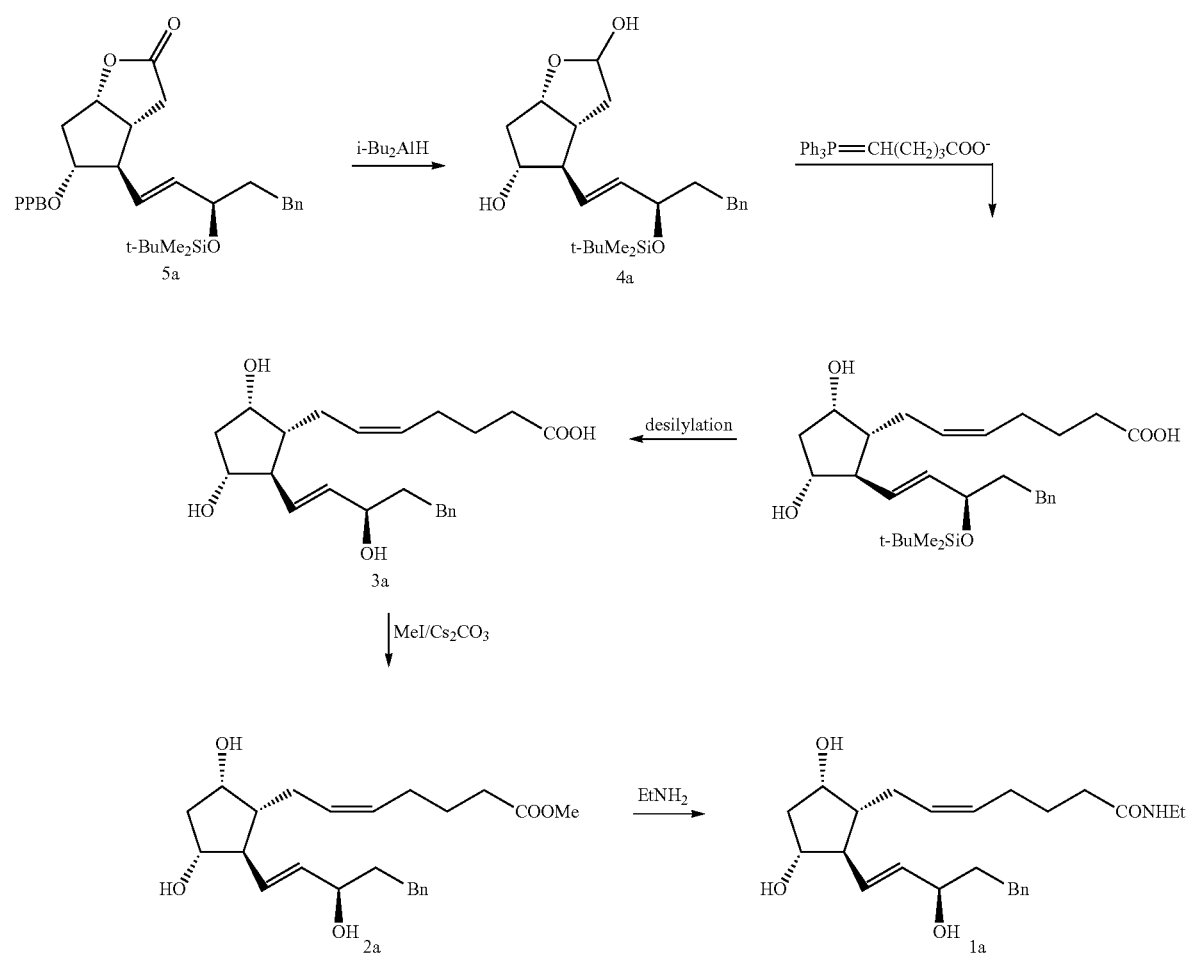

5-trans Bimatoprost 1b was prepared from methyl ester 2 according to Scheme 5.

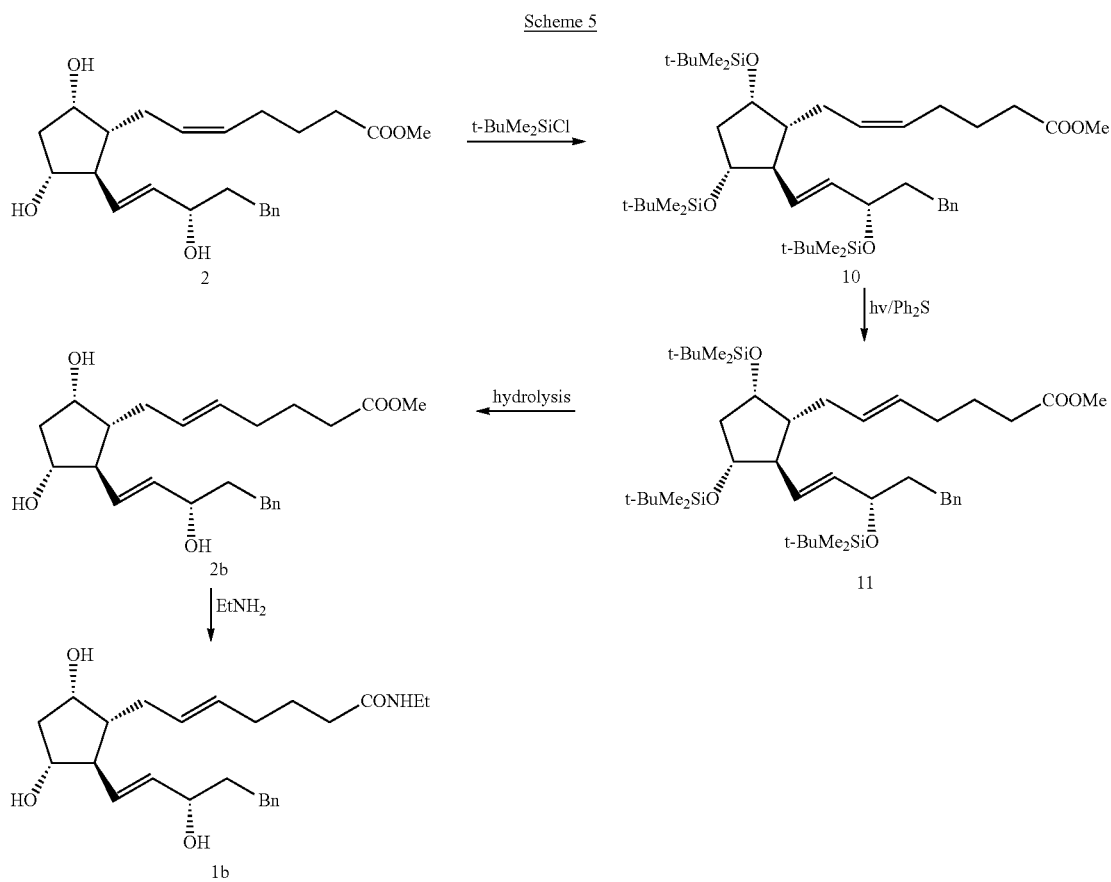

Scheme 5

The key step of the synthesis is isomerisation of methyl ester 10 to its 5-trans isomer 11 by irradiation in the presence of Ph$_2$S.

15-keto Bimatoprost 1c was prepared by selective oxidation of 15-hydroxy group of bimatoprost.

It has been found that the 5-trans and 15R-isomers of bimatoprost are particularly difficult to remove because they have similar physical and chemical properties to bimatoprost. We found that it is possible to separate of bimatoprost from the impurities using an HPLC purification system. However the HPLC purification is expensive and is not practical for large scale separations.

These problems have been solved by the use of crystalline form I in purification of bimatoprost. The present invention provides a method for purifying crude bimatoprost from related impurities, which comprises the steps of:
a) dissolving crude bimatoprost in an organic solvent or a mixture of organic solvent and anti-solvent under reflux conditions;
b) allowing the hot solution to cool;
c) separating the precipitate from the supernatant solution;
d) drying the resulting solid in vacuo at low temperature and then at 30 to 40° C. to give bimatoprost crystalline form I with desired LC purity.

By using the process of the present invention, it has been found possible to produce bimatoprost that is substantially free of 15R- and 5-trans isomers of bimatoprost. Using the process of the present invention, bimatoprost containing less than 0.2% each of 15R- and 5-trans isomers can be produced. In particular, bimatoprost containing less than 0.1% each of 15R- and 5-trans isomers can be produced. Preferably, bimatoprost containing less than 0.05% each of 15R- and 5-trans isomers can be produced.

The above processes thus enable bimatoprost having an extremely high degree of purity can be obtained, e.g. greater than 98% pure, greater than 99% pure, greater than 99.5% pure. Indeed, it has been found possible to achieve bimatoprost purities of greater than 99.8%.

The present invention also provides the use of bimatoprost crystalline form I in the manufacture of a medicament. The medicament is prepared in two steps, preparation of a composition containing bimatoprost and manufacture of unit dosage forms suitable for pharmaceutical use, e.g. topical ocular use. Preferably, the composition is prepared by combining a therapeutically effective amount of bimatoprost crystalline form I, as an active ingredient, with conventional pharmaceutically-acceptable excipients, e.g. an ophthalmically-acceptable vehicle. The therapeutically efficient amount typically is between about 0.0001 and about 5% (w/v), preferably about 0.001 to about 1.0% (w/v) in liquid formulations.

In addition to the above-described principal active ingredients, the compositions of the present invention may further comprise various formulatory ingredients, such as ophthalmically acceptable diluents, buffers, hydrochloric acid, sodium hydroxide, antimicrobial preservatives, stabilizers, tonicity adjustors, viscosity-enhancing agents, chelating agents, antioxidants, surfactants and/or solubilizers and combinations thereof.

Preferably, the diluent is purified water.

Preservatives are used in multi-use ophthalmic formulations to prevent microbial contamination of the composition after the packaging has been opened. A number of preservatives have been used including quaternary ammonium salts, mercury compounds, alcohols and stabilized chlorine dioxide. Preferred preservatives that may be used in the pharmaceutical compositions of the present invention include benzalkonium chloride, chlorobutanol, thimerosal, phenylmercuric acetate, methyl paraben, propyl paraben, phenylethyl alcohol, edetate disodium, sorbic acid, phenylmercuric nitrate, Polyquad™.

Viscosity-enhancing agents may be added as needed or convenient. They include, but are not limited to, sodium carboxymethylcellulose, hydroxypropylmethylcellulose, povidone, polyvinyl alcohol, polyethylene glycol, or combinations thereof.

Tonicity adjustors may be added as needed or convenient. They include, but are not limited to, salts, particularly sodium chloride, potassium chloride, mannitol, dextrose, propylene glycol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Hydrochloric acid or sodium hydroxide may be used to adjust the pH of these formulations as needed.

Preferred surfactants are, for example, polyethoxylated castor oil, Tween 80, polyvinyl alcohol, povidone, hydroxypropyl methyl cellulose, poloxamers, carboxymethyl cellulose and hydroxyethyl cellulose cyclodextrin.

Other excipient components, which may be included in the ophthalmic preparations, are chelating agents. The preferred chelating agent is edetate disodium, although other chelating agents may also be used in place of or in conjunction with it.

The following abbreviations are used:
(−)-DIP-Chloride™ (Sigma-Aldrich)=(−)-B-chlorodiisopinocampheylborane
Bn=benzyl;
br.=broad;
Bu=n-butyl;
i-Bu=i-butyl;
d=doublet;
DBU=1,8-diazabicyclo[5.4.0]undec-7-ene;
i-Bu$_2$AlH=diisobutylaluminium hydride;
DMAP=4-N,N-dimethylaminopyridine;
DMF=N,N-dimethylformamide;
DMSO=dimethyl sulfoxide;
DRIFTS=diffuse reflectance infrared Fourier-transform spectrum (spectroscopy);
DSC=differential scanning calorimetry;
FT-IR=Fourier-transform infrared;
GC=gas chromatography;
HPLC=high performance liquid chromatography;
HMPA=hexamethylphosphoramide;
INN=International Nonproprietary Name;
IOP=intraocular pressure;
i-PrOH=isopropanol;
IR=infrared;
LC=liquid chromatography;
m=multiplet;
MTBE=tert-butyl methyl ether;
NMT=not more than;
NMP=1-methyl-2-pyrrolidinone;
NMR=nuclear magnetic resonance;
PPB=4-phenylbenzoyl;
PPTS=pyridinium p-toluenesulfonate;
rt=room temperature;
s=singlet;
t=triplet;
THF=tetrahydrofuran;
TGA=thermogravimetric analysis;
USAN=United States Adopted Name;
XRPD=x-ray powder diffraction.

The following example is illustrative, but not limiting, of the methods of the present invention. Other suitable modifications and adaptations of the variety of conditions and parameters normally encountered in chemical synthesis and which are obvious to those skilled in the art are within the spirit and scope of the invention.

EXAMPLES

Experimental Details:

All reagents and solvents were purchased from Aldrich Chemical Company unless specified otherwise and used without further purification. All reactions were provided under argon or nitrogen atmosphere.

The LC purity was determined by separating a sample by High performance liquid chromatography (HPLC) and calculating the area percentage thereof of each peak. The chromatographic analysis of bimatoprost is based on a chiral reversed-phase HPLC method with an optically active tris(3, 5-dimethylphenylcarbamate) of cellulose immobilized on silica support stationary phase and a mobile phase buffered at pH 4.5. HPLC method was carried out using a 10 □m Chiralpak™ OD-R 250×4.6 mm column (Diacel). Diluent—mixture A/B 25:75, sample concentration—about 0.5 mg per 1 mL, injection volume—20 µL; a mobile phase—gradient A/B 25:75 for 0 min, 25:75 for 25 min, 35:65 for 35 min, 35:65 for 60 min, 25:75 for 65 min, 25:75 for 80 min wherein A is MeCN and B is Et$_3$N (1.0 mL) solution in water (1 L), pH adjusted with 85% H$_3$PO$_4$ up to 4.5. Column temperature 35° C.; a flow rate of 0.7 mL/min; and a UV detector at 200 nm.

NMR spectra were recorded on a Bruker AM-200 ($^1$H at 200 MHz, $^{13}$C at 50 MHz) and Bruker AM-400 ($^1$H at 400 MHz) instruments using CDCl$_3$ (unless otherwise stated) as a solvent, and chemical shifts are in δ (ppm) relative to internal TMS.

Infrared (IR) absorption spectra were obtained by Nicolet Impact 410 FT-IR spectrophotometer using a dispersion of solid sample material in KBr or Nujol. Infrared DRIFTS spectra were obtained by Nicolet Impact 410 FT-IR spectrophotometer equipped with Pike Technologies EasiDiff Diffuse Reflectance Accessory using a dispersion of solid sample material in KBr.

Powder x-ray diffraction patterns were obtained by methods known in the art using PANALYTICAL (Philips) X'Pert Pro MPD x-ray powder diffraction system (CuK$_\alpha$ radiation, PW3050/60 goniometer, PW3015/20 X'Celerator detector). The Bragg-Brentano scheme was used for beam focusing.

Melting points were determined in open capillary tubes with Buchi B-545 capillary melting point apparatus or Mettler-Toledo FP-900 Thermosystem with FP-81 HT Melting Point Cell and FP-90 central processor, or Electrothermal IA 9300 digital melting point apparatus, and are uncorrected. The melting points generally depend on the purity level of the samples. Typically, bimatoprost crystalline form I has been found to have a melting point between 62 and 64° C.

Measurements of difference between the temperature of a sample and a reference pan that are subject to the same temperature program (differential scanning calorimetry, DSC) were obtained on a Mettler-Toledo DSC 822e Differential Scanning Calorimeter.

Example 1

(3aR,4R,5R,6aS)-4-(3-Oxo-5-phenyl-1E-pentenyl)-5-(4-phenylbenzoyloxy)-hexahydro-2H-cyclopenta[b]furan-2-one

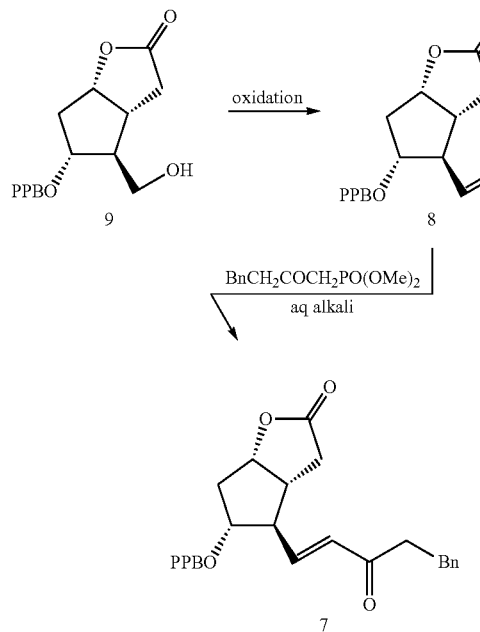

A solution of (−)-Corey lactone 5-(4-phenylbenzoate) 9 (17.6 g, 50.0 mmol) and TEMPO (0.16 g, 1.0 mmol) in $CH_2Cl_2$ (100 mL) was added to a solution of NaBr (0.5 g, 5.0 mmol), $NaHCO_3$ (12.6 g, 150.0 mmol) and IPA (6.0 g, 100.0 mmol) in water (100 mL). 5% aq. NaOCl (about 150 mL) was added dropwise to the stirred mixture at −5 to 0° C. until disappearance of Corey lactone (TLC monitoring). The obtained mixture was stirred for 0.5 h at the same temperature. The aqueous layer was separated and extracted with $CH_2Cl_2$ (50 mL). The combined organic layers was added dropwise over 1 h to a stirred mixture of a solution of $BnCH_2COCH_2PO(OMe)_2$ (15.4 g, 60.0 mmol) in $CH_2Cl_2$ (20 mL) and 30% NaOH (8.0 g, 60.0 mmol) at 0-5° C. The mixture was stirred 0.5 h at the same temperature and treated with 10% aq. citric acid (100 mL). The aqueous layer was separated and extracted with $CH_2Cl_2$ (50 mL). The combined organic layers were dried over $Na_2SO_4$, filtered through short silica gel column and concentrated in vacuo. The oily residue (24.2 g) was dissolved in refluxed EtOH (150 mL) and cooled in ice bath. The precipitate was filtered off, washed with cold EtOH and dried in vacuo to give 20.1 g (84%) of ketone 7 with 99.4% purity by HPLC: mp 129-130° C., $[\alpha]^{20}_D$ −142° (c 1.0, $CHCl_3$); $^1$H NMR ($CDCl_3$) ☐ 2.32-2.63 (m, 3H); 2.84-2.97 (m, 7H); 5.00-5.10 (m, 1H); 5.20-5.35 (m, 1H); 6.20 (d, J=16 Hz, 1H); 6.65 (dd, J=16 and 8 Hz, 1H); 7.15-7.67 (m, 12H); 8.03 (d, J=8 Hz, 2H).

Example 2

(3aR,4R,5R,6aS)-4-[3R- and 3S-hydroxy-5-phenyl-1E-pentenyl]-5-(4-phenylbenzoyloxy)-hexahydro-2H-cyclopenta[b]furan-2-ones (mixture of 3R- and 3S-isomers)

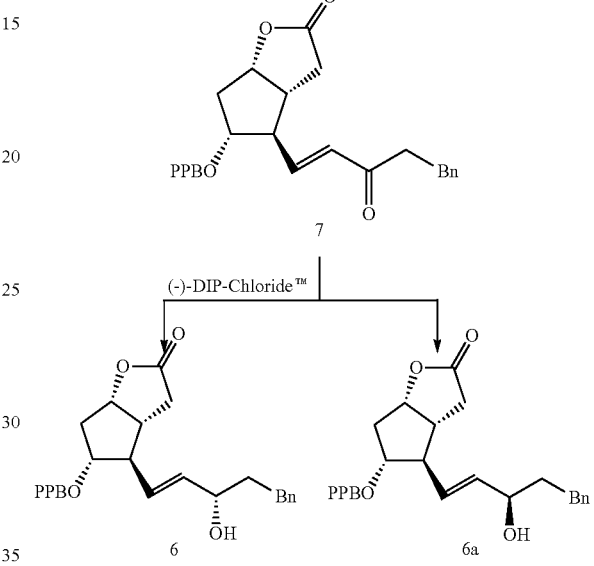

A solution of (−)-DIP-Chloride™ (77.0 g, 0.24 mol) in $CH_2Cl_2$ (150 mL) was added dropwise during 2 h to a stirred solution of ketone 7 (57.7 g, 0.12 mol) in $CH_2Cl_2$ (300 mL) at −25 to −30° C. The mixture was stirred overnight at the same temperature and treated with MeOH (100 mL) at rt. The obtained mixture was stirred for 0.5 h and washed with 20% aq. $NH_4Cl$ (250 mL). The aqueous layer was separated and extracted with $CH_2Cl_2$ (2×100 mL). The combined organic layers were dried over $Na_2SO_4$, filtered and concentrated in vacuo. The residue was crystallized from MeOH to give 49.8 g (86%) of mixture alcohols 6 and 6a with 6/6a ratio about 97:3 by HPLC.

Example 3

(3aR,4R,5R,6aS)-4-[3S-(t-Butyldimethylsiloxy)-5-phenyl-1E-pentenyl]-5-(4-phenylbenzoyloxy)-hexahydro-2H-cyclopenta[b]furan-2-one 5

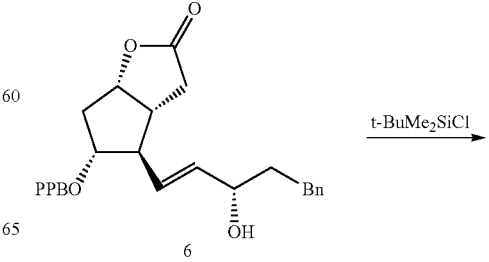

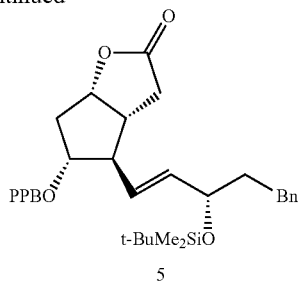

A mixture of alcohols 6 and 6a with 6/6a ratio about 97:3 by HPLC (15.4 g, 32.0 mmol), CH$_2$Cl$_2$ (75 mL), t-BuMe$_2$SiCl (7.2 g, 48.0 mmol) and imidazole (6.5 g, 96.0 mmol) was refluxed for 1 h and mixed with 10% aq. citric acid (50 mL). The aqueous layer was separated and extracted with CH$_2$Cl$_2$ (50 mL). The combined organic layers were dried over Na$_2$SO$_4$, filtered through the column with silica gel (30 g) and concentrated in vacuo. The residue was crystallized from MTBE to give 16.2 g (76%) of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one 5 as MTBE solvate with 99.8% purity by HPLC: mp 60-64° C.; [α]$^{20}_D$-84° (c 1, MeCN); $^1$H NMR (CDCl$_3$) □ 8.04 (d, J=8 Hz, 2H), 7.60 (m, 4H), 7.42 (m, 3H), 7.15 (m, 5H), 5.58 (m, 2H), 5.22 (q, J=5.5 Hz, 1H), 5.01 (t, J=5.5 Hz, 1H), 4.12 (q, J=5.5 Hz, 1H), 3.18 (s, 3H), 2.69 (m, 7H), 2.20 (m, 1H), 1.79 (m, 2H), 1.17 (s, 9H), 0.85 (s, 9H), −0.02 (d, J=12 Hz, 6H).

The x-ray powder diffraction pattern of crystalline MTBE solvate of compound 5 has characteristic peaks expressed in degrees 2θ at approximately 6.5, 7.1, 12.2, 12.5, 13.1, 13.6, 14.6, 15.0, 15.8, 16.2, 16.3, 17.0, 17.3, 18.0, 18.2, 18.8, 19.5, 19.7, 20.5, 20.8, 21.0, 21.8, 22.2, 23.0, 23.3, 24.2, 25.5, 26.5 and 26.7.

IR DRIFTS (KBr): 2949, 2931, 2854, 1765, 1715, 1607, 1361, 1266, 1203, 1170, 1118, 1095, 1080, 972, 912, 852, 839, 775, 745, and 699 cm$^{-1}$.

Compound 5 MTBE solvate was characterized by $^1$H NMR (CDCl$_3$), powder x-ray diffractometry, IR DRIFTS (KBr) spectroscopy, DSC and TGA as set forth above and in FIGS. 6, 7, 8, 9 and 10.

Example 4

Preparation of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one 5 and (3aR,4R,5R,6aS)-4-[3R-(t-butyldimethylsilyloxy)-5-phenyl-1E-pentenyl]-5-(4-phenylbenzoyloxy)-hexahydro-2H-cyclopenta[b]furan-2-one 5a

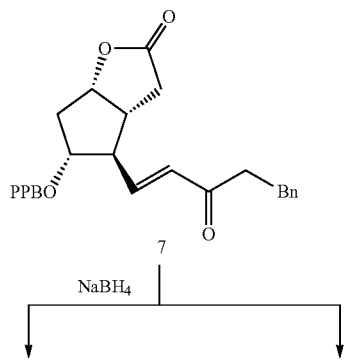

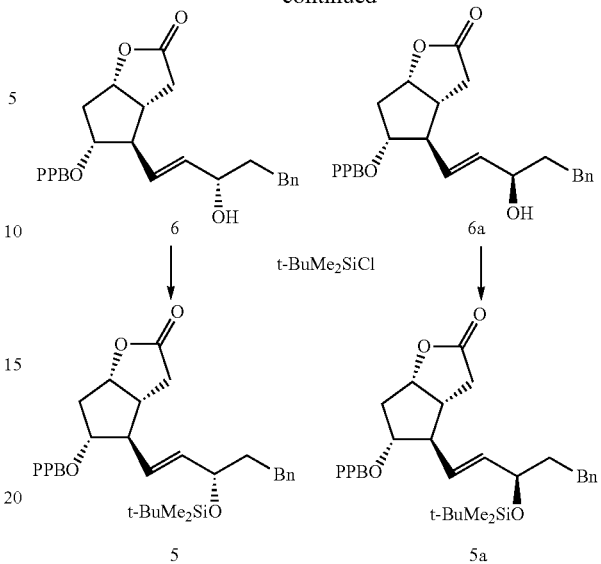

NaBH$_4$ (1.7 g, 44 mmol) was added in three portions to a stirred mixture of ketone 7 (21.0 g, 43.7 mmol), CH$_2$Cl$_2$ (125 mL) and MeOH (125 mL) at 0-4° C. during 1 h. The obtained mixture was stirred for 1 h at 0-4° C. and concentrated in vacuo. A mixture of the residue, CH$_2$Cl$_2$ (200 mL) and 5% NaHCO$_3$ (100 mL) was stirred for 1 h at 25° C. The aqueous phase was separated and extracted with CH$_2$Cl$_2$ (50 mL). The combined organics were washed with 5% NaHCO$_3$ (30 mL), dried over Na$_2$SO$_4$, filtered and concentrated in vacuo to give 20.0 g (95%) of mixture 6 and 6a with ratio 6/6a~1:1.

A solution of the residue (20.0 g, 41.4 mmol) and imidazole (4.3 g, 62.2 mmol) in CH$_2$Cl$_2$ (200 mL) was treated with a solution of t-BuMe$_2$SiCl (7.5 g, 49.7 mmol) in CH$_2$Cl$_2$ (30 mL). The resulted suspension was refluxed for 2 h, cooled to 10° C. and quenched by addition of 10% aq citric acid (60 mL). The phases were separated, the organic one was washed with water (100 mL) and 10% NaHCO$_3$ (30 mL), dried over Na$_2$SO$_4$, filtered and passed through silica gel (30 g). The column was washed with CH$_2$Cl$_2$ (300 mL) and the combined filtrates were evaporated under reduced pressure to give 25.0 g of mixture 5 and 5a with ratio 5/5a~1:1. The residue (25 g) was crystallized from MTBE (100 mL) to give 9.3 g of crude lactone 5 MTBE solvate (0.6% of 5a) as white solid. The crude product was re-crystallized from MTBE (80 mL) affording 8.5 g (30% from ketone 7) of lactone 5 MTBE solvate (0.02% of 5a) as white crystalline powder. mp 60-64° C.; [α]$^{20}_D$-84° (c 1, MeCN).

All filtrates were combined and concentrated in vacuo. A mixture of the residue (18.0 g), heptane (165 mL) and toluene (15 mL) was stirred for 0.5 h at 70° C. and for 12 h at rt. The precipitate was filtered off, washed with heptane on the filter and dried in vacuo to give 8.0 g of crude lactone 5a preferably (4% of 5). Two additional crystallizations of the crude product afforded 6.0 g (24% from ketone 7) of lactone 5a as white crystalline powder with 99.7% purity (0.2% of 5) by HPLC, mp 93-94° C. and [α]$_D^{20}$-92° (c 1, CHCl$_3$).

All filtrates were combined again, evaporated and treated as described above to give additionally 2.8 g (10% from ketone 7) of lactone 5 MTBE solvate and 2.2 g (9% from ketone 7) of lactone 5a. Total 11.3 g (40% from ketone 7) of lactone 5 MTBE solvate and 8.2 g (33% from ketone 7) of lactone 5a was prepared.

(3aR,4R,5R,6aS)-4-[3S-(t-Butyldimethylsiloxy)-5-phenyl-1E-pentenyl]-5-(4-phenylbenzoyloxy)-hexahydro-2H-cyclopenta[b]furan-2-one MTBE solvate was characterized by $^1$H NMR (CDCl$_3$), powder x-ray diffractometry, IR DRIFTS (KBr) spectroscopy, DSC and TGA as set forth above and in FIGS. 6-10.

(3aR,4R,5R,6aS)-4-[3R-(t-butyldimethylsiloxy)-5-phenyl-1E-pentenyl]-5-(4-phenylbenzoyloxy)-hexahydro-2H-cyclopenta[b]furan-2-one 5a: H$^1$ NMR (200 MHz) δ 8.00 (d, 2H, J 8.3 Hz), 7.58 (m, 4H), 7.35 (m, 3H), 7.15 (m, 3H), 7.06 (t, 2H, J 7.1 Hz), 5.60 (m, 2H), 5.22 (dd, 1H, J$_1$ 6.1 Hz, J$_2$ 12.0 Hz), 5.04 (dd, J$_1$ 4.3 Hz, J$_2$ 12.0 Hz), 4.11 (q, 1H, J 5.8 Hz), 2.85-2.44 (m, 7H), 2.20 (m, 1H), 1.73 (m, 2H), 0.85 (m, 9H), −0.02 (d, 6H, J 7.3 Hz)

The x-ray powder diffraction pattern of crystalline (3aR, 4R, 5R,6aS)-4-[3R-(t-butyldimethylsiloxy)-5-phenyl-1E-pentenyl]-5-(4-phenylbenzoyloxy)-hexahydro-2H-cyclopenta[b]furan-2-one 5a has characteristic peaks expressed in degrees 2θ at approximately 5.7, 6.3, 14.0, 14.5, 14.8, 15.5, 16.3, 17.0, 17.5, 17.8, 18.1, 18.6, 18.9, 19.3, 21.5, 22.0, 22.4 and 23.8. IR (KBr): 3428.8, 3061.1 3027.7, 2952.1, 2928.7, 2884.0, 2855.8, 1761.7, 1714.4, 1608.2, 1487.6, 1471.1, 1454.3, 1404.6, 1360.1, 1313.0, 1276.0, 1181.3, 1114.1, 1082.5, 1061.0, 1006.6, 974.3, 901.8, 869.0, 836.1, 776.6, 748.2, 698.6, and 670.0 cm$^{-1}$.

Lactone 5a was characterized by $^1$H NMR (CDCl$_3$), powder x-ray diffractometry, DSC, and IR (KBr) spectroscopy as set forth above and illustrated in FIGS. 11-14.

Example 5

Preparation of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one 5

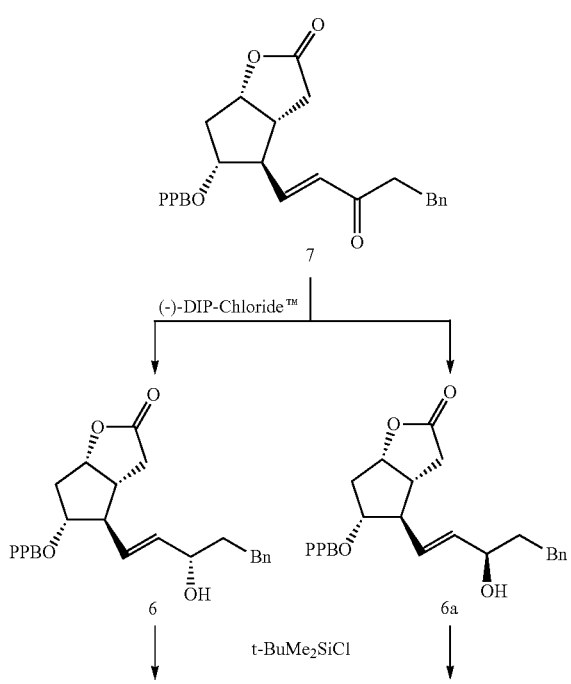

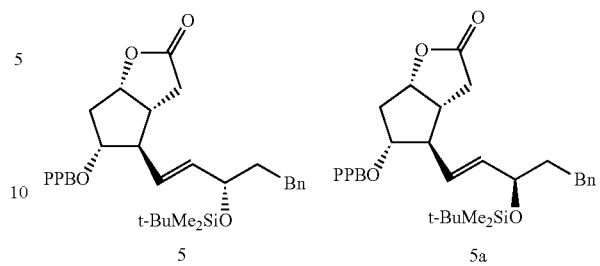

A solution of (−)-DIP-Chloride™ (282.3 g, 0.88 mol) in CH$_2$Cl$_2$ (500 mL) was added dropwise during 2 h to a stirred solution of ketone 7 (210.0 g, 0.44 mol) in CH$_2$Cl$_2$ (1.6 L) at −25 to −30° C. The mixture was stirred 12 h at the same temperature, heated to −3° C. and treated with 10% aq. NH$_4$Cl (400 mL). The obtained mixture was stirred for 1 h at rt. The aqueous layer was separated and extracted with CH$_2$Cl$_2$ (2×150 mL). The combined organic layers were dried over Na$_2$SO$_4$, filtered and concentrated in vacuo to a half of volume. A mixture of the residue and imidazole (179.8 g, 2.64 mol) was treated with a solution of t-BuMe$_2$SiCl (265.3 g, 1.76 mol) in CH$_2$Cl$_2$ (500 mL). The resulted suspension was refluxed for 2 h, cooled to 10° C. and quenched by addition of 10% aq citric acid (1.5 L). The phases were separated, the organic one was washed with water (300 mL) and 10% NaHCO$_3$ (300 mL), dried over Na$_2$SO$_4$, filtered and passed through silica gel (250 g). The column was washed with CH$_2$Cl$_2$ (2 L) and the combined filtrates were evaporated under reduced pressure. The residue (350 g) was crystallized from MTBE (2.4 L) to give 232.0 g of crude lactone 5 MTBE solvate (0.6% of 5a) as white solid. The crude product was re-crystallized from MTBE (2 L) affording 217 g (72% from ketone 7) of lactone 5 MTBE solvate (0.02% of 5a) as white crystalline powder.

Example 6

(3aR,4R,5R,6aS)-4-(3S-hydroxy-5-phenyl-1E-pentenyl)-5-hydroxy-hexahydro-2H-cyclopenta[b]furan-2-one 6

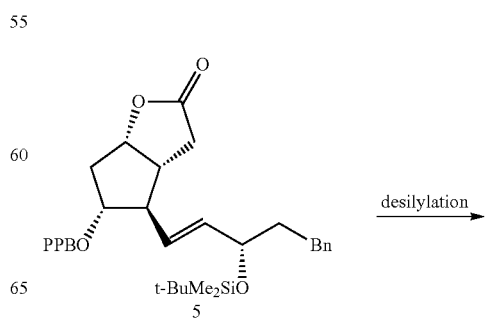

37.6; 38.7; 42.7; 54.1; 71.6; 79.0; 83.1; 125.9; 127.1; 127.2; 128.2; 128.3; 128.8; 128.9; 130.1; 136.2; 139.9; 141.5; 146.1; 165.9; 176.2.

Example 8

(3aR,4R,5R,6aS)-4-(3-oxo-5-phenyl-1E-pentenyl)-5-hydroxy-hexahydro-2H-cyclopenta[b]furan-2-one 7

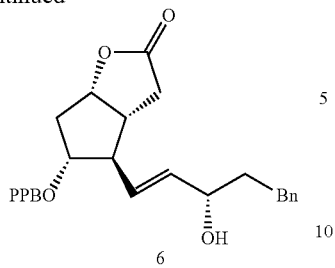

6

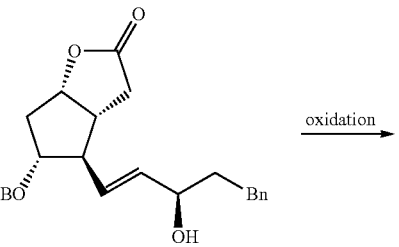

Method A. A mixture of compound 5 MTBE solvate (0.69 g, 1.2 mmol), 1 M solution of Bu₄NF in THF (1.4 mL, 1.4 mmol) and THF (4 mL) was stirred for 3 h at rt and treated with water (20 mL). The obtained mixture was extracted with MTBE. The combined organic extracts were dried over $Na_2SO_4$, filtered and concentrated in vacuo. The residue was crystallized from MeOH to give alcohol 6 as white crystals with mp 126-128° C.: ¹H NMR (CDCl₃) is in agreement with the structure.

Method B. A mixture of compound 5 MTBE solvate (1.0 g, 1.7 mmol), 32% HCl (0.1 mL, 0.3 mmol) and MeOH (6 mL) was stirred for 2 h at 40° C. and for 2 h at 0 to 5° C. The precipitate was filtered off, washed on the filter with cold MeOH and dried in vacuo to give alcohol 6 as white crystals.

Example 7

(3aR,4R,5R,6aS)-4-(3R-hydroxy-5-phenyl-1E-pentenyl)-5-hydroxy-hexahydro-2H-cyclopenta[b]furan-2-one 6a

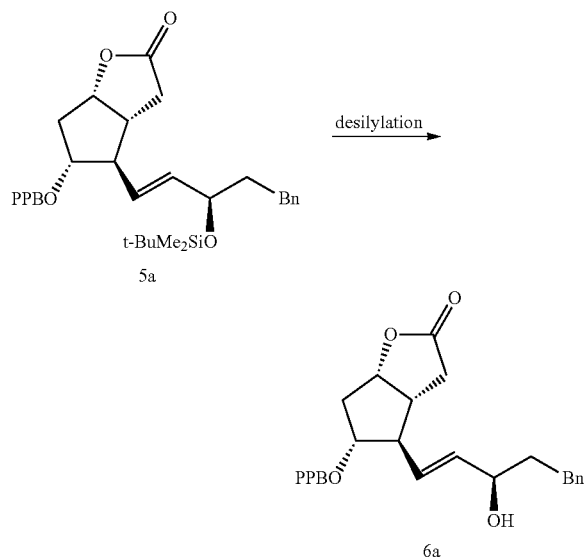

Cleavage of silyl-protective group of compound 5a following by column chromatography purification on silica gel gives alcohol 6a as white crystals with mp 81-83° C. (Et₂O/hexane): $[\alpha]_D^{20}$ −124.5° (c 1, MeCN); ¹H NMR (CDCl₃) δ: 7.08-8.05 (m, 14H); 5.51-5.74 (m, 2H); 5.21-5.30 (m, 1H); 5.02-5.07 (m, 1H); 4.09-4.13 (m, 1H); 2.46-2.92 (m, 7H); 2.18-2.28 (m, 1H); 1.66-1.86 (m, 3H). ¹³C (CDCl₃) δ: 31.6; 34.8;

Method A. A solution of C₅H₅N.SO₃ (0.32 g) in DMSO (3.5 mL) was added dropwise to a stirred solution of alcohol 6a (0.30 g) and Et₃N (0.40 g) in CH₂Cl₂ (4 mL) at −5 to 0° C. The mixture was stirred at the same temperature for 1 h (TLC monitoring) and poured into cold water (15 mL). The mixture was stirred for 10 min at 0-5° C. The organic layer was separated, the water layer was extracted with CH₂Cl₂ (3×5 mL). The combined organic layers were washed with brine (3×10 mL), dried over Na₂SO₄, filtered and evaporated under reduced pressure. A solution of the residue in MeOH (1 mL) was cold to −10° C. and kept at the same temperature for 3 h. The precipitated crystals were filtered, washed on filter with cold MeOH (2×1 mL) and dried under reduced pressure to a constant weight to give 0.26 g (87% yield) of crude ketone 7 with 94% purity by HPLC. The crude ketone 7 was recrystallized from MeOH gave crystalline ketone 7 with mp 134-135° C. and $[\alpha]_D^{20}$ −141.7° (c 1.26, MeCN).

Method B. 5% aq. NaOCl (40 mL, TLC monitoring) was added dropwise to a stirred mixture of alcohol 6a (0.53 g, 1.1 mmol), TEMPO (4 mg, 0.025 mmol), NaBr (12 mg, 0.12 mmol), NaHCO₃ (0.3 g, 3.6 mmol), CH₂Cl₂ (3 mL) and water (3 mL) at rt and the mixture was stirred for 1 h. The aqueous layer was separated and extracted with CH₂Cl₂ (3 mL). The combined organic layer was dried over Na₂SO₄ and filtered trough short silica gel column. The residue was concentrated in vacuo and crystallized from MeOH (5 mL) to give 0.37 g (70%) of ketone 7.

Example 9

(3aR,4R,5R,6aS)-4-[3S-(t-butyldimethylsiloxy)-5-phenyl-1E-pentenyl]-5-hydroxy-hexahydro-2H-cyclopenta[b]furan-2-ol 4

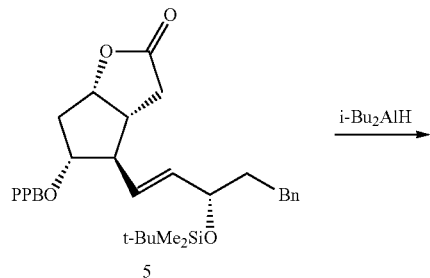

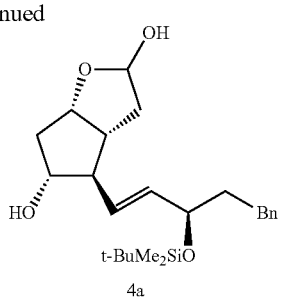

i-Bu$_2$AlH (20% w/w solution in toluene, 59.5 mL, 72 mmol) was added dropwise to a stirred solution of lactone 5 MTBE solvate (15.0 g, 21.8 mmol) in toluene (100 mL) at −25 to −20° C. The mixture was stirred for 1 h at the same temperature, heated to −10° C. and quenched by slow addition of 10% aq citric acid (210 g, 109 mmol) keeping reaction temperature below 20° C. The resulted suspension was stirred for 1 h at rt until most of solids disappeared. The aqueous phase was separated and extracted with toluene (50 mL). The combined organics were washed with 5% NaHCO$_3$ (50 mL), dried over Na$_2$SO$_4$, filtered and passed through silica gel column (80 g). The column was eluted with CH$_2$Cl$_2$ (1 L) and then with the mixture CH$_2$Cl$_2$/EtOAc 1:1 (1 L), the fractions containing lactol 4 were combined and concentrated in vacuo to give 9.0 g (99%) of lactol 4 with 98.5% purity by HPLC.

Example 10

(3aR,4R,5R,6aS)-4-[3R-(t-butyldimethylsiloxy)-5-phenyl-1E-pentenyl]-5-hydroxy-hexahydro-2H-cyclopenta[b]furan-2-ol 4a

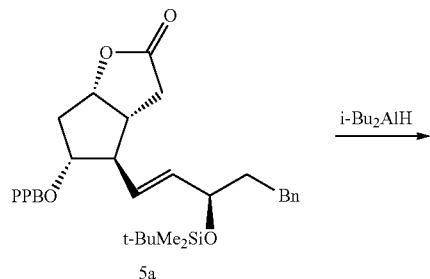

i-Bu$_2$AlH (20% w/w in toluene, 50 mL, 60.0 mmol) was added dropwise to a stirred solution of lactone 5a (10.74 g, 18.0 mmol) in toluene (70 mL), at −25 to −15° C. The mixture was stirred at the same temperature for 2 h, then heated to −10° C. and quenched by slow addition of 10% aq citric acid (173 mL, 90.0 mmol). The resulted mixture was stirred for 1 h at rt until the most of solids were disappeared. The aqueous phase was separated and extracted with toluene (50 mL). The combined organics were washed with 5% NaHCO$_3$ (50 mL), dried over Na$_2$SO$_4$, filtered and passed through silica gel column (60 g). The column was eluted with CH$_2$Cl$_2$ (1 L) and then with the mixture CH$_2$Cl$_2$/EtOAc 1:1 (1 L), the fractions containing the lactol 4a were combined and concentrated in vacuo to give 7.5 g ( %) of lactol 4a as viscous oil with 98.5% purity by HPLC.

Example 11

Bimatoprost acid 3

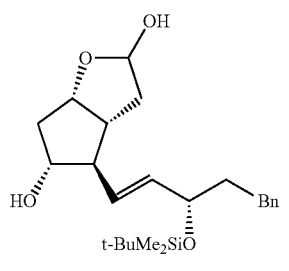

1. Ph$_3$P═CH(CH$_2$)$_3$COO$^−$;
2. hydrolysis

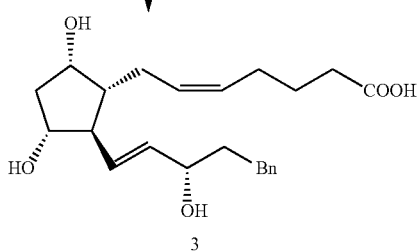

t-BuOK (19.4 g, 172.0 mmol) was added in three portions to a mixture of HOOC(CH$_2$)$_4$PPh$_3{}^+$ Br$^−$ (38.3 g, 86.0 mmol) and THF ( mL) at −5 to 0° C. The obtained mixture was stirred for 0.5 h at the same temperature and a solution of lactol 4 (9.0 g, 21.5 mmol) in dry THF (50 mL) was slowly added. The mixture was stirred for 10 h at 0 to 5° C. and quenched by addition of water (200 mL). The pH of the mixture was adjusted to 7.5-8.0 with 20% aq citric acid, most of THF was evaporated in vacuo and extracted with MTBE (3×150 mL). The combined organics were washed with 5% NaHCO₃ (adjusted to pH 8 with 20% aq citric acid, 2×100 mL) and brine, and concentrated in vacuo. The residue was dissolved in MeOH (80 mL), the solution was cooled to 0° C., and 3 N HCl (21.5 mL, 64.5 mmol) was slowly added keeping reaction temperature below 10° C. The resulted mixture was stirred for 5 h at 0 to 5° C. and quenched by addition of 10% NaOH (44 g, 110 mmol). The mixture was stirred for 1 h at 40° C., most of MeOH was evaporated in vacuo and the aqueous phase was extracted with MTBE (4×70 mL). The combined organics were washed with 10% NaOH (40 mL), the aqueous layers were combined and acidified to pH 3.5-4.5 with 20% aq citric acid. The resulted mixture was extracted with MTBE (3×100 mL), the combined organics were washed with brine, dried over Na₂SO₄, filtered and passed through silica gel column (45 g). The column was eluted with MTBE (500 mL) and EtOAc (800 mL), the fractions containing bimatoprost acid were combined and concentrated in vacuo to give 7.5 g (90%) of bimatoprost acid 3 as slight yellow semisolid mass. Analytical HPLC showed that the product contained about 3.5% of the 5-trans isomer (from the Wittig reaction).

Example 12

15R-Bimatoprost acid 3a

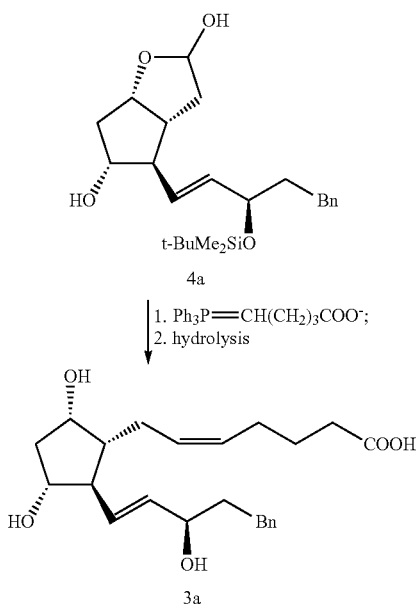

t-BuOK (16.2 g, 144.0 mmol) was added in three portions to a stirred mixture of HOOC(CH₂)₄PPh₃⁺ Br⁻ (31.9 g, 72.0 mmol) and THF ( mL) at −5° C. The mixture was stirred for 0.5 h at −3° C. and a solution of lactol 4a (7.5 g, 18.0 mmol) in dry THF (50 mL) was slowly added. The mixture was stirred for 10 h at 0° C. and quenched by addition of water (200 mL). The pH of the mixture was adjusted to 7.5-8.0 with 20% aq citric acid, the most of THF was evaporated and the aqueous mixture was extracted with MTBE (3×120 mL). The combined organics were washed with 5% NaHCO₃ (adjusted to pH 7.7-8.0 with 20% aq citric acid, 2×30 mL) and brine and concentrated in vacuo. A solution of the residue in MeOH (50 mL) was treated with 3 N HCl (15 mL) at 0° C. The resulted mixture was stirred for 4 h at 0-4° C. and quenched by addition of 10% NaOH (44 mL). The mixture was stirred for 1 h at 40° C., the most of MeOH was evaporated in vacuo and the aqueous phase was extracted with MTBE (4×70 mL). The combined organics were washed with 10% NaOH (30 mL), the aqueous layers were combined and acidified to pH 3.5-4.5 with 20% aq citric acid. The resulted mixture was extracted with MTBE (3×100 mL), the combined organics were washed with brine, dried over Na₂SO₄, filtered and passed through silica gel column (60 g). The column was eluted with CH₂Cl₂ (300 mL), CH₂Cl₂/EtOAc 1:1 (300 mL) and EtOAc (600 mL), the fractions containing 3a were combined and concentrated in vacuo to give 4.6 g (65%) of 15R-bimatoprost acid 3a as yellow oil.

Example 13

Methyl ester of bimatoprost acid 2

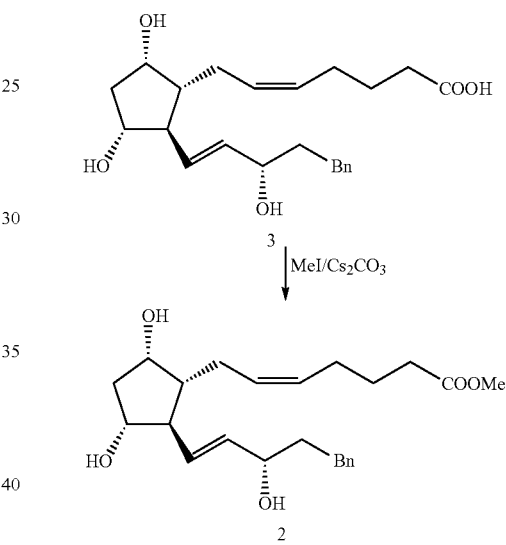

A mixture of bimatoprost acid 3 (7.5 g, 19.3 mmol), MeI (1.8 mL, 29.0 mmol), Cs₂CO₃ (7.6 g, 23.2 mmol) and DMF (50 mL) was stirred for 4 h at 0 to 4° C., acidified to pH 4 with 3% aq citric acid, heated to rt and extracted with MTBE (3×70 mL). The combined organics were washed with 5% NaHCO₃ (50 mL), dried over Na₂SO₄, filtered and concentrated in vacuo to give 7.6 g (98%) of ester 2 as oil.

Example 14

Methyl ester of 15R-bimatoprost acid 2a

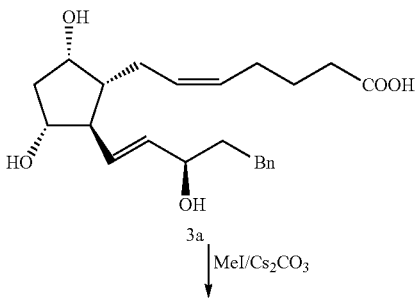

-continued

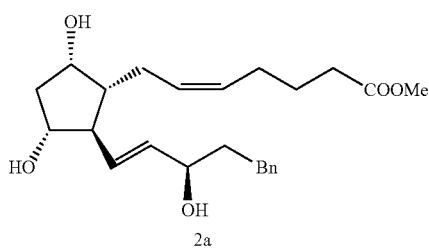
2a

A mixture of acid 3a (4.3 g, 11.0 mmol), MeI (2.3 g, 16.0 mmol), $Cs_2CO_3$ (5.2 g, 16.0 mmol) and DMF (30 mL) was stirred for 4 h at 0-4° C., acidified to pH 4 with 3% aq citric acid (120 mL), heated to rt and extracted with MTBE (3×40 mL). The combined organics were washed with 5% $NaHCO_3$ (50 mL), dried over $Na_2SO_4$, filtered and concentrated in vacuo The residue was purified by chromatography on silica gel (30 g, eluted with $CH_2Cl_2$, $CH_2Cl_2$/EtOAc 1:1, 300 mL and then EtOAc 600 mL) to give 4.0 g (91%) of ester 2a as oil.

Example 15

15R-Bimatoprost 1a

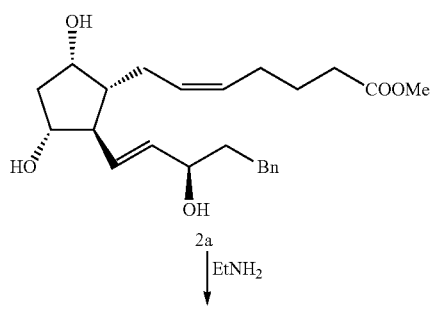
1a

A mixture of ester 2a (3.0 g, 7.5 mmol), 70% aq $EtNH_2$ (15 mL, 189 mmol) and MeOH (15 mL) was stirred for 72 h at rt in well-closed flask and concentrated in vacuo. The oil residue was portioned between EtOAc (100 mL) and water (60 mL). The aqueous phase was separated and extracted with EtOAc (30 mL). The combined organics were washed with 10% $NaHCO_3$ (2×30 mL) and brine, dried over $Na_2SO_4$, filtered and concentrated in vacuo. The residue was purified by chromatography on a silica gel column (30 g, eluted with EtOAc then EtOAc/MeOH 10:1) to give 2.4 g (79%) of 15R-bimatoprost 1a as light yellow viscous oil.

Example 16

Methyl ester of tri(tert-butyldimethylsilyl) bimatoprost acid 10

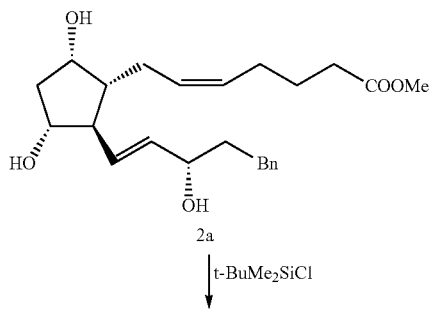
10

A mixture of ester 2a (3.30 g, 8.2 mmol), imidazole (5.58 g, 82.0 mmol) and t-$BuMe_2SiCl$ (6.18 g, 41.0 mmol) in DMF (20 mL) was stirred overnight at rt and the reaction was quenched by addition of 10% aq citric acid (100 mL). The mixture was extracted with MTBE (3×30 mL), the combined organics were washed with a 10% $NaHCO_3$ (30 mL), dried over $Na_2SO_4$, filtered and concentrated in vacuo. The residue was purified on a silica gel (70 g, eluted with heptane, then heptane/EtOAc 10:1) to give 6.01 g (98%) of ester 10 as light oil.

Example 17

Methyl ester of tri(tert-butyldimethylsilyl)-5-trans bimatoprost acid 11

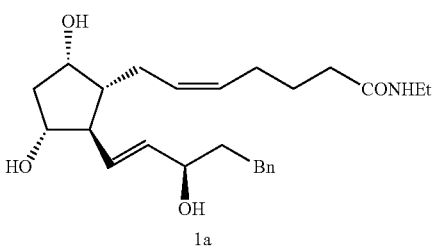
10

$\downarrow$ hv/$Ph_2S_2$

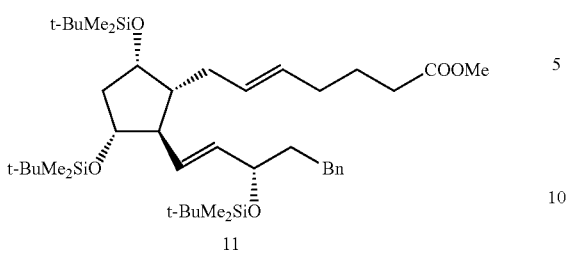

A mixture of ester 10 (6.00 g, 8.0 mmol) and Ph$_2$S$_2$ (0.35 g, 0.16 mmol) in toluene (60 mL) was irradiated with 400 W halogen lamp under reflux conditions for 8 h and concentrated in vacuo. The residue was purified on a silica gel (70 g, eluted with heptane, then heptane/EtOAc 10:1) to give 5.51 g of mixture trans- and cis-isomers with ratio about 4 to 1. This mixture was separated on a silica gel modified with AgNO$_3$ (24.0 g of AgNO$_3$ on 200.0 g of silica gel, eluted with heptane then heptane/toluene 50:1) to give 3.85 g (70%) of ester 11 as transparent viscous oil.

Example 18

Methyl ester of 5-trans bimatoprost acid 2b

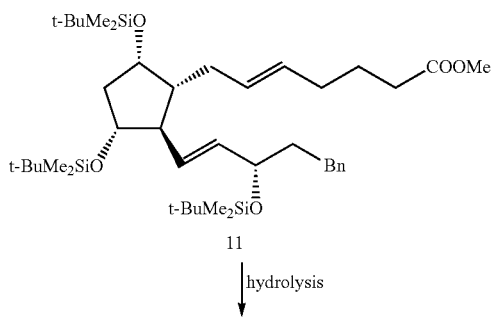

A mixture of ester 2b (3.73 g, 5.0 mmol) and Bu$_4$NF (1 M solution in THF, 25 mL, 25.0 mmol) was stirred 14 h at rt and concentrated in vacuo. A solution of the residue in CH$_2$Cl$_2$ was washed with 10% aq citric acid, dried over Na$_2$SO$_4$, filtered and concentrated in vacuo. The residue was purified by chromatography on a silica gel (30 g, eluent CH$_2$Cl$_2$, then CH$_2$Cl$_2$/EtOAc 1:1) to give 1.65 g (82%) of ester 2b.

Example 19

5-trans Bimatoprost 1b

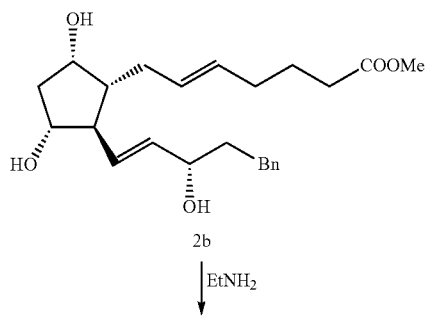

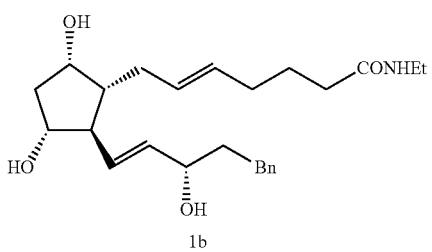

A solution of ester 2b (1.21 g, 3.0 mmol) in the mixture of MeOH (8 mL) and 70% aq EtNH$_2$ (8 mL, 101 mmol) was stirred in the well-closed flask for 72 h at rt. The volatiles were removed under reduced pressure and the oil residue was dissolved in CH$_2$Cl$_2$ and purified on a silica gel (30 g, eluent EtOAc then EtOAc/MeOH 10:1) to give 1.03 g (83%) of 5-trans bimatoprost 1b as light yellow viscous oil.

Example 20

15-keto Bimatoprost 1c

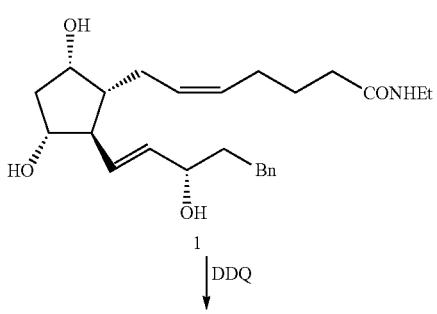

-continued

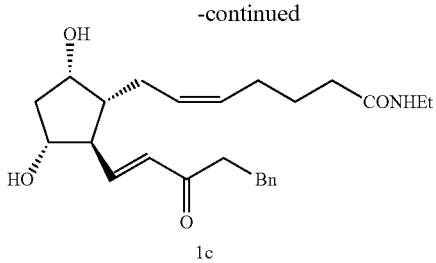

1c

A mixture of bimatoprost 1 (0.33 g, 0.8 mmol), DDQ (0.68 g, 3.0 mmol), CH$_2$Cl$_2$ (5 mL) and 1,4-dioxane (5 mL) was stirred for 24 h at 40° C. and evaporated in vacuo. The residue was purified by chromatography on a silica gel (20 g, eluent EtOAc then EtOAc/MeOH 20:1) to give 0.21 g (63%) of 15-keto bimatoprost 1c as yellow oil.

Example 21

Bimatoprost form I

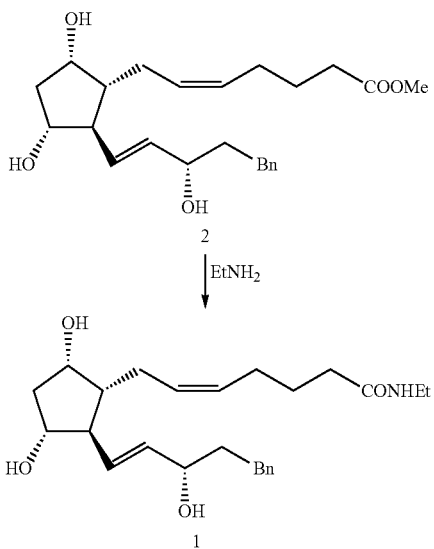

A mixture of ester 2 [9.0 g, 22.4 mmol, contain (by HPLC) 3.5% of 5-trans isomer], 70% aq EtNH$_2$ (40 mL, 503 mmol) and MeOH (45 mL) was stirred in a well closed flask at 24 to 27° C. for 72 h and concentrated in vacuo. The residue was portioned between EtOAc (100 mL) and water (60 mL). The phases were separated, the aqueous one was extracted with EtOAc (30 mL) and the combined organics were washed with 10% NaHCO$_3$ (2×30 mL) and brine, dried over Na$_2$SO$_4$, filtered and concentrated in vacuo to give 8.0 g (86%) of crude bimatoprost containing 3.5% (by HPLC) of 5-trans isomer 1b. The crude bimatoprost was crystallized from a mixture of EtOAc (27 mL) and MTBE (54 mL) as follows: dissolving the crude bimatoprost at or near the boiling point and allowing the hot solution to cool to rt. Additional MTBE (40 mL) was added and the mixture was stirred for 2 h at 0 to 5° C. The precipitate was filtered off, washed on the filter with cold MTBE (2×20 mL) and dried in vacuo for 1 h at 0 to 5° C., for 0.5 h at rt and for 2 h at 30 to 40° C. to give 7.5 g (80%) of bimatoprost crystalline form I as white solid with 98% purity by HPLC, less than 1% of 5-trans isomer 1b. The bimatoprost (7.5 g) was crystallized from EtOAc (75 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 6.7 g (90% recovery) of bimatoprost crystalline form I as white powder with 99% purity by HPLC, 0.6% 5-trans isomer 1b, NMT 0.1% of 15R-isomer 1a, and NMT 0.1% of 15-keto bimatoprost 1c; mp 64-66° C.; $[\alpha]_D^{20}$+ 36° (c 1, MeOH).

The x-ray powder diffraction pattern of bimatoprost crystalline form I has characteristic peaks expressed in degrees 2θ at approximately 5.4, 6.2, 10.9, 11.3, 13.7, 16.6, 17.5, 18.3, 18.6, 18.9, 19.4, 19.7, 19.9, 20.7, 20.9, 21.6, 22.7 and 28.2.

IR DRIFTS (KBr): 3426.6, 3390.7, 3320.8, 3083.3, 3059.3, 3010.8, 2911.8, 2863.8, 1618.1, 1544.8, 1495.6, 1453.5, 1370.0, 1344.6, 1316.0, 1289.1, 1259.9, 1247.9, 1150.6, 1096.4, 1053.4, 1026.3, 975.0, 919.7, 767.4, 746.0, 728.1, 697.7, 607.2 and 597.6 cm$^{-1}$.

IR (KBr): 3414.9, 3326.6, 3085.5, 3025.1, 3011.5, 2929.6, 2914.2, 2864.9, 1644.8, 1619.2, 1546.2, 1496.2, 1454.6, 1372.9, 1346.0, 1317.3, 1290.4, 1260.9, 1249.3, 1229.4, 1203.6, 1151.9, 1097.2, 1054.5, 1028.6, 975.4, 920.5, 767.6, 747.5, 721.7, 698.9, 596.2, 545.9, 491.2 and 463.0 cm$^{-1}$.

IR (Nujol): 3418.5, 3328.2, 3085.2, 3062.4, 2953.1, 2925.4, 2854.7, 1619.6, 1545.3, 1496.3, 1456.5, 1376.5, 1346.2, 1316.5, 1290.0, 1261.0, 1248.7, 1229.1, 1203.3, 1151.1, 1122.6, 1097.5, 1054.6, 1027.1, 975.9, 961.0, 920.3, 768.1, 721.8, 697.8, 595.7 and 545.4 cm$^{-1}$.

Crystalline form I of bimatoprost was characterized by powder x-ray diffractometry, DSC, IR DRIFTS (KBr), IR (KBr) and IR (Nujol) spectroscopy as set forth above and illustrated in FIGS. 1-5.

Example 22

Purification of Crude Bimatoprost

Crude bimatoprost containing (by HPLC) 2% to 5% 5-trans isomer was dissolved in mixture of EtOAc and MTBE at or near the boiling point. The solution was slowly cooled to 0-5° C. The precipitate was filtered and dried in vacuo for 1 h at 0 to 5° C., for 0.5 h at rt and for 2 h at 30 to 40° C. to give crystalline bimatoprost form I, containing (by HPLC) not more than 1% of 5-trans isomer. Repeated crystallization procedures give crystalline bimatoprost form I as white powder with not less than 99% purity (by HPLC), containing not more than 0.5% of 5-trans isomer, not more than 0.1% of 15R-isomer 1a, and not more than 0.1% of 15-keto bimatoprost 1c.

Example 23

Crystalline Form I of Bimatoprost

Bimatoprost with 98% purity (by HPLC), contain 1% of 5-trans isomer (0.5 g) was crystallized from isopropylacetone (10 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.4 g (80% recovery) of bimatoprost crystalline form I as white powder with 99% purity (by HPLC), containing 0.6% of 5-trans isomer.

Example 24

Crystalline Form I of Bimatoprost

Bimatoprost with 98% purity (by HPLC), contain 1% of 5-trans isomer (0.5 g) was crystallized from t-BuOAc (9 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.45 g (90% recovery) of bimatoprost crystalline form I as white powder with 99.2% purity (by HPLC), containing 0.6% of 5-trans isomer.

Example 25

Crystalline Form I of Bimatoprost

Bimatoprost with 98% purity (by HPLC), contain 1% of 5-trans isomer (0.7 g) was crystallized from BuOAc (5 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.6 g (86% recovery) of bimatoprost crystalline form I as white powder with 99.4% purity (by HPLC), containing 0.5% of 5-trans isomer.

Example 26

Crystalline Form I of Bimatoprost

Bimatoprost with 98.5% purity (by HPLC), contain 0.8% of 5-trans isomer (0.5 g) was crystallized from EtOAc (5 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.45 g (90% recovery) of bimatoprost crystalline form I as white powder with 99.3% purity (by HPLC), containing 0.5% of 5-trans isomer, 0.05% of 15R-isomer and 0.01% of 15-keto bimatoprost.

Example 27

Crystalline Form I of Bimatoprost

Bimatoprost form A (prepared according to US2005/209337, 0.3 g) was crystallized from mixture of EtOAc (1.5 mL) and MTBE (3 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.25 g (83% recovery) of bimatoprost crystalline form I as white powder.

Example 28

Crystalline Form I of Bimatoprost

Bimatoprost (0.4 g) was crystallized from mixture of MeOH (0.5 mL) and MTBE (10 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.3 g (75% recovery) of bimatoprost crystalline form I as white powder.

Example 29

Crystalline Form I of bimatoprost

Bimatoprost (0.5 g) was crystallized from mixture of t-BuOH (3 mL) and heptane (5 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.35 g (70% recovery) of bimatoprost crystalline form I as white powder.

Example 30

Crystalline Form I of Bimatoprost

A mixture of oily bimatoprost (prepared according to U.S. Pat. No. 5,352,708, 1.0 g) and ether (20 mL) was stirred for 0.5 h at or near the boiling point, slowly cooled to 0-5° C. The precipitate was filtered and dried in vacuo for 1 h at 0 to 5° C., for 0.5 h at rt and for 2 h at 30 to 40° C. to give 0.94 g (94% recovery) of bimatoprost crystalline form I as white powder.

Example 31

Crystalline Form I of Bimatoprost

A mixture of bimatoprost (0.4 g) and heptane (10 mL) was stirred at 70° C. for 2 h, slowly cooled to 0-5° C., filtered and dried in vacuo for 1 h at 0 to 5° C., for 0.5 h at rt and for 2 h at 30 to 40° C. affording 0.38 g (95% recovery) of bimatoprost crystalline form I as white solid.

Example 32

Crystalline Form I of Bimatoprost

Bimatoprost (0.4 g) was crystallized from toluene (6 mL) as follows: dissolving the bimatoprost at 70° C., allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.38 g (95% recovery) of bimatoprost crystalline form I as white powder.

Example 33

Crystalline Form I of Bimatoprost

Bimatoprost form A containing 2.5% (by HPLC) of 5-trans isomer (0.3 g) was crystallized from EtOAc (1.5 mL) and MTBE (3 mL) as follows: dissolving the bimatoprost at or near the boiling point, allowing the hot solution to cool to rt, keeping the mixture for 1 h at rt and for 2 h at 0 to 5° C. The precipitate was filtered off and dried in vacuo for 1 h at 0 to 5° C., for 0.5 h at rt and for 2 h at 30 to 40° C. to give 0.25 g (83% recovery) of bimatoprost crystalline form I as white powder with 99.0% purity by HPLC, 0.8% trans-isomer.

Example 34

Crystalline Form I of Bimatoprost

Bimatoprost (0.53 g) was crystallized from $CH_2Cl_2$ (3.0 g) as follows: dissolving the bimatoprost at or near the boiling point, allowing the hot solution to cool to rt, keeping the mixture for 1 h at rt and for 2 h at 0 to 5° C. The precipitate was filtered off, washed on the filter with cold (0 to 5° C.) CH$_2$Cl$_2$ (2.0 g) and dried in vacuo for 1 h at 0 to 5° C., for 0.5 h at rt and for 2 h at 30 to 40° C. to give 0.31 g (59% recovery) of bimatoprost crystalline form I.

Example 35

Crystalline Form I of Bimatoprost

Bimatoprost (0.53 g) was crystallized from isobutyl methyl ketone (15.06 g) as follows: dissolving the bimatoprost at 60° C., allowing the hot solution to cool to rt, keeping the mixture for 1 h at rt and for 2 h at 0 to 5° C. The precipitate was filtered off, washed on the filter with cold (0 to 5° C.) isobutyl methyl ketone (2.0 g) and dried in vacuo for 1 h at 0 to 5° C., for 0.5 h at rt and for 2 h at 30 to 40° C. to give 0.52 g (98% recovery) of bimatoprost crystalline form I.

Example 36

Crystalline Form I of Bimatoprost

Bimatoprost (0.50 g) was crystallized from t-BuOMe (71.7 g) as follows: dissolving the bimatoprost at or near the boiling point, allowing the hot solution to cool to rt, keeping the mixture for 1 h at rt and for 2 h at 0 to 5° C. The precipitate was filtered off, washed on the filter with cold (0 to 5° C.) t-BuOMe (2.0 g) and dried in vacuo for 1 h at 0 to 5° C., for 0.5 h at rt and for 2 h at 30 to 40° C. to give 0.52 g (98% recovery) of bimatoprost crystalline form I.

Example 37

Crystalline Form I of Bimatoprost

Bimatoprost (0.46 g) was crystallized from toluene (70.92 g) as follows: dissolving the bimatoprost at 70° C., allowing the hot solution to cool to rt, keeping the mixture for 1 h at rt and for 2 h at 0 to 5° C. The precipitate was filtered off, washed on the filter with cold (0 to 5° C.) toluene (2.0 g) and dried in vacuo for 1 h at 0 to 5° C., for 0.5 h at rt and for 2 h at 30 to 40° C. to give 0.30 g (65% recovery) of bimatoprost crystalline form I.

Example 38

Crystalline Form I of Bimatoprost

Bimatoprost (0.52 g) was crystallized from MeCN (10.6 g) as follows: dissolving the bimatoprost at or near the boiling point, allowing the hot solution to cool to rt, keeping the mixture for 1 h at rt and for 2 h at 0 to 5° C. The precipitate was filtered off, washed on the filter with cold (0 to 5° C.) MeCN (2.0 g) and dried in vacuo for 1 h at 0 to 5° C., for 0.5 h at rt and for 2 h at 30 to 40° C. to give 0.43 g (83% recovery) of bimatoprost crystalline form I.

Example 39

Crystalline Form I of Bimatoprost

Bimatoprost (0.51 g) was crystallized from EtOAc (8.1 g) as follows: dissolving the bimatoprost at or near the boiling point, allowing the hot solution to cool to rt, keeping the mixture for 1 h at rt and for 2 h at 0 to 5° C. The precipitate was filtered off, washed on the filter with cold (0 to 5° C.) EtOAc (2.0 g) and dried in vacuo for 1 h at 0 to 5° C., for 0.5 h at rt and for 2 h at 30 to 40° C. to give 0.42 g (82% recovery) of bimatoprost crystalline form I.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. Crystalline form I of bimatoprost, which exhibits an x-ray powder diffraction pattern consisting essentially of characteristic peaks, expressed in degrees 2θ at about 5.4±0.2, 10.9±0.2, 11.3±0.2, 13.7±0.2, 16.6±0.2, 17.5±0.2, 19.9±0.2, 20.7±0.2 and 22.7±0.2 as shown in FIG. 1.

2. Crystalline form according to claim 1, wherein said bimatoprost is free of other physical forms.

3. Crystalline form according to claim 1, having a melting point of 62 to 64° C.

4. Crystalline form of bimatoprost according to claim 1, wherein said bimatoprost contains (by HPLC) not more than (NMT) 2% of sum of all related impurities and 1% of 5-trans isomer.

5. Crystalline form of bimatoprost according to claim 1, wherein said bimatoprost contains (by HPLC) not more than (NMT) 1.5% of sum of all related impurities and 0.7% of 5-trans isomer.

6. Crystalline form of bimatoprost according to claim 1, wherein said bimatoprost contains (by HPLC) not more than (NMT) 1% of sum of all related impurities and 0.5% of 5-trans isomer.

7. Crystalline form of bimatoprost according to claim 1, wherein said bimatoprost is substantially free of 5-trans and 15(R)-isomers of bimatoprost.

8. Crystalline form of bimatoprost according to claim 1, wherein said bimatoprost contains by LC not more than (NMT) 0.2% each of 5-trans isomer and 15(R) isomer.

9. Crystalline form of bimatoprost according to claim 1, wherein said bimatoprost contains by LC not more than (NMT) 0.1% each of 5-trans isomer and 15(R) isomer.

10. Crystalline form of bimatoprost according to claim 1, wherein said bimatoprost contains by LC not more than (NMT) 0.05% each of 5-trans isomer and 15(R) isomer.

11. A process of producing crystalline form I of bimatoprost according to claim 1, wherein said process comprises the steps of:
  a) dissolving crude bimatoprost in an organic solvent or a mixture of organic solvent and anti-solvent at or near the boiling point, wherein said organic solvent is selected from the group consisting of methanol, ethanol, isopropanol, butanol, isobutanol, t-butanol, ethyl acetate, isopropyl acetate, butyl acetate, acetone, methyl ethyl ketone, isopropylacetone, dichloromethane, chloroform, chlorobenzene or mixture thereof, and wherein said anti solvent is selected from the group of pentane, hexane, heptane, cyclohexane, diethyl ether, diisopropyl ether and t-BuOMe;
  b) allowing the hot solution to cool;
  c) separating the precipitate from the supernatant solution;
  d) drying the resulting solid in vacuo at 0 to 5 °C. and then at 30 to 40° C. to give crystalline form I of bimatoprost.

12. A process of producing crystalline form I of bimatoprost according to claim 1, wherein said bimatoprost is free from other physical forms, said process comprises the steps of:
  a) dissolving crude bimatoprost in an organic solvent or a mixture of organic solvent and anti-solvent at or near the boiling point, wherein said organic solvent is selected from the group consisting of methanol, ethanol, isopropanol, butanol, isobutanol, t-butanol, ethyl acetate, isopropyl acetate, butyl acetate, acetone, methyl ethyl ketone, isopropylacetone, dichloromethane, chloroform, chlorobenzene or mixture thereof, and wherein said anti solvent is selected from the group of pentane, hexane, heptane, cyclohexane, diethyl ether, diisopropyl ether and t-BuOMe;
  b) allowing the hot solution to cool;
  c) separating the precipitate from the supernatant solution;
  d) drying the resulting solid in vacuo at 0 to 5 ° C. and then at 30 to 40° C. to give crystalline form I of bimatoprost free from other physical forms.

13. The process of claim 11, wherein said crystalline form I of bimatoprost is obtained in a purity greater than 98%.

14. The process of claim 11, wherein said crystalline form I of bimatoprost is obtained in a purity greater than 99.5%.

15. The process of claim 12, wherein said crystalline form I of bimatoprost is obtained in a purity greater than 98%

16. The process of claim 13, wherein said crystalline form I of bimatoprost is obtained in a purity greater than 99.5% .

17. A process of producing bimatoprost according to claim 1, said process comprises the steps of:
  a) dissolving crude bimatoprost in an organic solvent or a mixture of organic solvent and anti-solvent at or near the boiling point;
  b) allowing the hot solution to cool;
  c) separating the precipitate from the supernatant solution;
  d) drying the resulting solid in vacuo at 0 to 5 ° C. and then at 30 to 40° C. to give bimatoprost at a purity greater than 98%.

18. A method for preparing the pharmaceutical composition for treating ocular hypertension by combining therapeutically effective amount of said bimatoprost according to claim 1 with ophthalmically-acceptable vehicle.

19. The method according to claim 18, wherein said ophthalmically-acceptable vehicle is selected from the group consisting of ophthalmically acceptable diluents, buffers, hydrochloric acid, sodium hydroxide, preservatives, stabilizers, tonicity adjustors, viscosityenhancing agents, chelating agents, surfactants and/or solubilizers and combinations thereof.

20. The method according to claim 19, wherein said diluent is purified water.

21. The method according to claim 19, wherein said surfactants are selected from the group consisting of polyethoxylated castor oil, Tween 80, polyvinyl alcohol, povidone, hydroxypropyl methyl cellulose, poloxamers, carboxymethyl cellulose, hydroxyethyl cellulose cyclodextrin, and combinations thereof.

22. The method according to claim 19, wherein said chelating agent is edentate disodium.

23. The method according to claim 19, wherein said buffers are selected from the group consisting of acetate buffers, citrate buffers, phosphate buffers, borate buffers, and combinations thereof.

24. The method according to claim 19, wherein said tonicity adjustors are selected from the group consisting of sodium chloride, potassium chloride, mannitol, dextrose, propylene glycol, glycerin, and combinations thereof.

25. The method according to claim 18, wherein said preservatives are selected from the group consisting of benzalkonium chloride, chlorobutanol, thimerosal, phenylmercuric acetate, methyl paraben, propyl paraben, phenylethyl alcohol, edetate disodium, sorbic acid, phenylmercuric nitrate, Polyquad™, stabilized chlorine dioxide, and combinations thereof.

26. The method according to claim 18, wherein said viscosity-enhancing agents are selected from the group consisting of sodium carboxymethylcellulose, hydroxypropylmethylcellulose, povidone, polyvinyl alcohol, polyethylene glycol, and combinations thereof.

27. A method of treating ocular hypertension in a subject by way of administering a pharmaceutical composition comprising said bimatoprost according to claim 1, to said subject.

* * * * *